US008940963B2

(12) United States Patent
Giritch et al.

(10) Patent No.: US 8,940,963 B2
(45) Date of Patent: Jan. 27, 2015

(54) PRODUCTION OF HETERO-OLIGOMERIC PROTEINS IN PLANTS

(75) Inventors: Anatoly Giritch, Halle/Saale (DE); Sylvestre Marillonnet, Halle/Saale (DE); Victor Klimyuk, Halle/Saale (DE); Yuri Gleba, Halle/Saale (DE)

(73) Assignee: Icon Genetics GmbH, Munich (DE)

( * ) Notice: Subject to any disclaimer, the term of this patent is extended or adjusted under 35 U.S.C. 154(b) by 1445 days.

(21) Appl. No.: 11/814,931

(22) PCT Filed: Jan. 27, 2006

(86) PCT No.: PCT/EP2006/000721
§ 371 (c)(1),
(2), (4) Date: Mar. 27, 2008

(87) PCT Pub. No.: WO2006/079546
PCT Pub. Date: Aug. 3, 2006

(65) Prior Publication Data
US 2009/0111145 A1    Apr. 30, 2009

Related U.S. Application Data

(60) Provisional application No. 60/593,606, filed on Jan. 28, 2005.

(30) Foreign Application Priority Data

Jan. 28, 2005   (EP) ................................ 05001819

(51) Int. Cl.
| C12N 15/83 | (2006.01) |
| C12N 15/13 | (2006.01) |
| C12P 21/08 | (2006.01) |
| C12N 15/84 | (2006.01) |
| C12N 15/82 | (2006.01) |
| C07K 14/59 | (2006.01) |

(52) U.S. Cl.
CPC ........ *C12N 15/8203* (2013.01); *C12N 15/8258* (2013.01); *C12N 15/8257* (2013.01); *C07K 14/59* (2013.01)
USPC ..................... 800/288; 435/320.1; 435/70.21; 435/468; 435/419; 536/23.53; 800/294; 800/317.3; 800/306; 800/312

(58) Field of Classification Search
None
See application file for complete search history.

(56) References Cited

U.S. PATENT DOCUMENTS

| 2003/0084482 A1* | 5/2003 | Hall et al. ..................... 800/288 |
| 2006/0085871 A1* | 4/2006 | Yusibov et al. ............... 800/280 |

FOREIGN PATENT DOCUMENTS

WO    WO 02/088369 A    11/2002

OTHER PUBLICATIONS

Verch et al 1998, Journal of Immunological Methods 220:69-75.*
Wright et al (Trends in Biotech, 151, pp. 26-32, 1997).*
Balogun et al (Fitopatol. Bras., 27(3), pp. 241-248, 2002).*
Vance et al (Virology, 206, pp. 583-590, 1995).*
Ko et al (PNAS, 100(13), pp. 8013-8018, 2003).*
Schillberg, S. et al., "Opportunities for recombinant antigen and antibody expression in transgenic plants-technology assessment," *Vaccine*, Nov. 18, 2004, pp. 1764-1769, vol. 23(15).
Verch, T. et al., "Expression and assembly of a full-length monoclonal antibody in plants using a plant virus vector,"*Journal of Immunological Methods*, Nov. 1, 1998, pp. 69-75. vol. 220(1-2).
Hendy, S. et al., "Rapid production of single-chain Fv fragments in plants using a potato virus X episomal vector,"*Journal of Immunological Methods*, Dec. 10, 1999, pp. 137-146, vol. 231(1-2).
McCormick, A. et al., "Rapid production of specific vaccines for lymphoma by expression of the tumor-derived single-chain Fv epitopes in tobacco plants,"*Proc. Natl. Acad. Sci. USA*, Jan. 19, 1999, pp. 703-708, vol. 96(2).
Gleba, Y. et al., "Magnification-a new platform for expressing recombinant vaccines in plants," Vaccine, Jan. 13, 2005, pp. 2042-2048, vol. 23(17-18).
Marillonnet, S. et al., "In planta engineering of viral RNA replicons: Efficient assembly by recombination of DNA modules delivered by Agrobacteium," *Natl. Academy of Science*, May 2004, pp. 6852-6857, vol. 101(18).
Canizares, M. et al., "Use of viral vectors for vaccine production in plants,"*Immunology and Cell Biology*, Jun. 2005, pp. 263-270, vol. 83(3).
Gleba, Y. et al., "Engineering viral expression vectors for plants: the "full virus" and the "deconstructed virus" strategies,"*Plant Biology*, Apr. 2004, pp. 182-188, vol. 7(2).
Vaquero, C. et al., "A carcinoembryonic antigen-specific diabody produced in tobacco,"*FASEB Journal*, Mar. 2002, pp. 408-410, vol. 16(3).
Vaquero, C. et al., "A carcinoembryonic antigen-specific diabody produced in tobacco,"*FASEB Journal Online*, Jan. 2002, Internet.
Ma, J. et al., "Antibody processing and engineering in plants, andnew strategies for vaccine production," Vaccine, Nov. 18, 2004, pp. 1814-1818, vol. 23(15).
Giritch, et al., "Rapid High-Yield Expression of Full-Size IgG Antibodies in Plants Coinfected with Noncompeting Viral Vectors," *PNAS*, Oct. 3, 2006, pp. 14701-14706, vol. 103, No. 40, The National Academy of Sciences, USA.

(Continued)

*Primary Examiner* — David T Fox
*Assistant Examiner* — Stephen Uyeno
(74) *Attorney, Agent, or Firm* — Alston & Bird LLP

(57) ABSTRACT

Process of producing in a plant, in plant tissue, or in plant cells a hetero-oligomeric protein comprising at least a first and a second protein subunit, said process comprising expressing in plant cells at least said first and said second protein subunit by (i) providing to said plant, said plant tissue or said plant cells a plus-sense single-stranded RNA viral vector encoding at least said first and said second protein subunit or (ii) providing to said plant, said plant tissue or said plant cells a first and a second plus-sense single-stranded RNA viral vector, said first viral vector encoding at least said first protein subunit, said second viral vector encoding at least said second protein subunit, whereby at least said first viral vector and said second viral vector are non-competing viral vectors.

28 Claims, 20 Drawing Sheets

(56) References Cited

OTHER PUBLICATIONS

Bendandi, M. et al., "Rapid high-yield production in plants of individualized idiotype vaccines for non-Hodgkin's lymphoma," *Annals of Oncology*, May 21, 2010, pp. 1-8, Oxford University Press.

Roy, G., et al., "A novel two-component *Tobacco mosaic virus*-based vector system for high-level expression of multiple therapeutic proteins including a human monoclonal antibody in plants," *Virology*, 2010, pp. 93-99, vol. 405, Elsevier.

Vezina, L., et al., "Transient co-expression for fast and high-yield production of antibodies with human-like N-glycans in plants," *Plant Biotechnology Journal*, 2009, pp. 442-455, vol. 7, Blackwell Publishing, Ltd.

\* cited by examiner

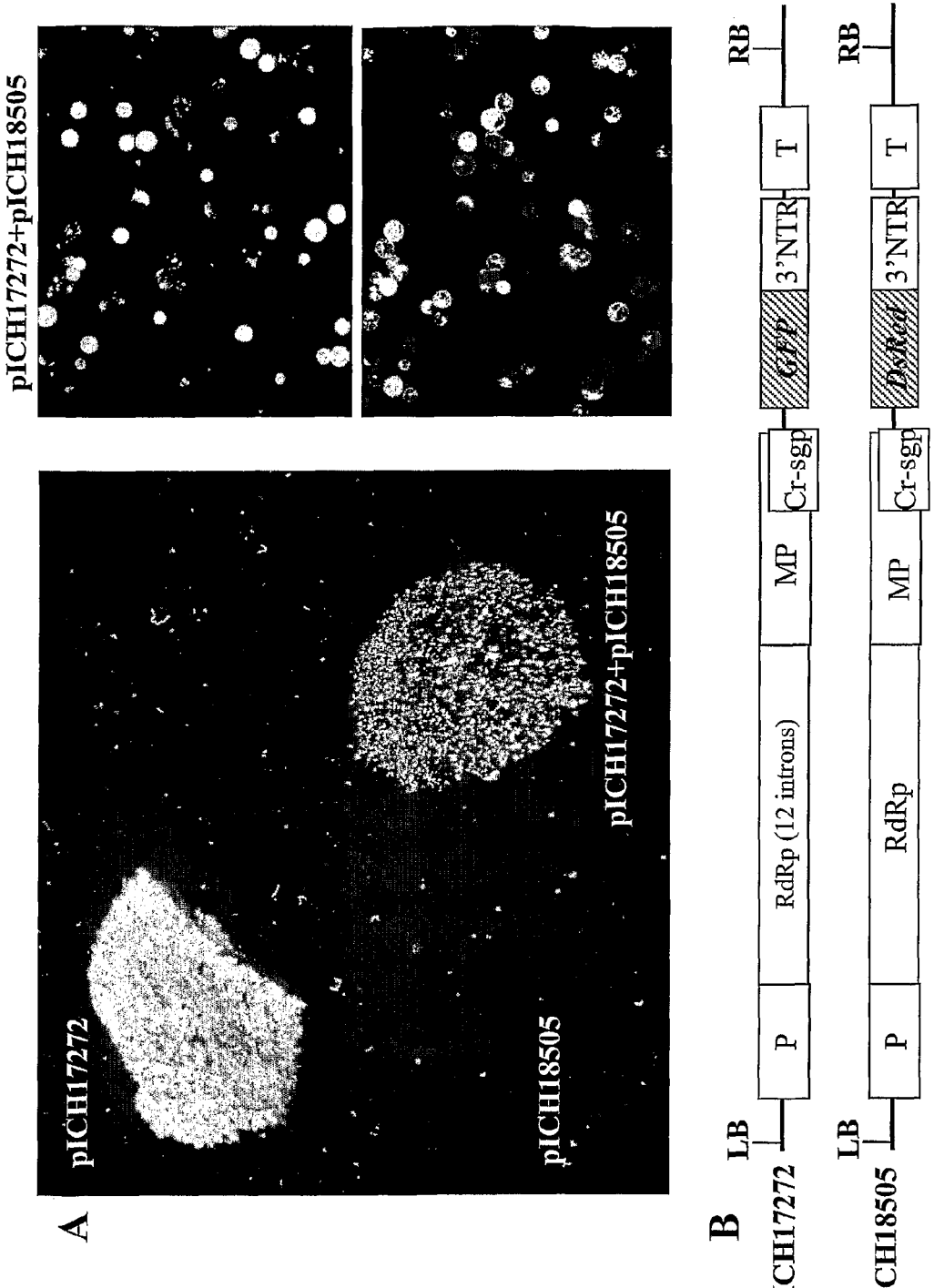
Figure 1(A,B)

SEQUENCE LISTING

```
<160> NUMBER OF SEQ ID NOS: 10

<210> SEQ ID NO 1
<211> LENGTH: 44
<212> TYPE: DNA
<213> ORGANISM: Artificial Sequence
<220> FEATURE:
<223> OTHER INFORMATION: PCR primer

<400> SEQUENCE: 1
tttggtctca tgaagaaaac taaaccatac accaccaaca caac            44

<210> SEQ ID NO 2
<211> LENGTH: 33
<212> TYPE: DNA
<213> ORGANISM: Artificial Sequence
<220> FEATURE:
<223> OTHER INFORMATION: PCR primer

<400> SEQUENCE: 2
```

```
cttttttccag cccggagacc atttctgtga tgg                                    33

<210> SEQ ID NO 3
<211> LENGTH: 39
<212> TYPE: DNA
<213> ORGANISM: Artificial Sequence
<220> FEATURE:
<223> OTHER INFORMATION: PCR primer

<400> SEQUENCE: 3
tttcgtctca gggctggaaa aagaggactt ccctgaagg                                39

<210> SEQ ID NO 4
<211> LENGTH: 28
<212> TYPE: DNA
<213> ORGANISM: Artificial Sequence
<220> FEATURE:
<223> OTHER INFORMATION: PCR primer

<400> SEQUENCE: 4
gagtcgtctc ctgcataaac ttgagcag                                           28

<210> SEQ ID NO 5
<211> LENGTH: 34
<212> TYPE: DNA
<213> ORGANISM: Artificial Sequence
<220> FEATURE:
<223> OTHER INFORMATION: PCR primer

<400> SEQUENCE: 5
tttgaagaca atgcaggaga cgactccgca ctgg                                    34

<210> SEQ ID NO 6
<211> LENGTH: 67
<212> TYPE: DNA
<213> ORGANISM: Artificial Sequence
<220> FEATURE:
<223> OTHER INFORMATION: PCR primer

<400> SEQUENCE: 6
cggacgtctt ttttttttt tttttttttt ttatttatat tattcataca atcaaaccag         60
aaaatac                                                                  67

<210> SEQ ID NO 7
<211> LENGTH: 40
<212> TYPE: DNA
<213> ORGANISM: Artificial Sequence
<220> FEATURE:
<223> OTHER INFORMATION: PCR primer

<400> SEQUENCE: 7
tttacgcgtt tcgacaaaat ttagaacgaa cttaattatg                              40

<210> SEQ ID NO 8
<211> LENGTH: 39
<212> TYPE: DNA
<213> ORGANISM: Artificial Sequence
<220> FEATURE:
<223> OTHER INFORMATION: PCR primer

<400> SEQUENCE: 8
tttggtctca ttcattcaaa gcggagagga aaatatatg                               39

<210> SEQ ID NO 9
<211> LENGTH: 31
```

```
<212> TYPE: DNA
<213> ORGANISM: Artificial Sequence
<220> FEATURE:
<223> OTHER INFORMATION: PCR primer

<400> SEQUENCE: 9
cagctagcaa caaacaagaa aggtaagttt c                                    31

<210> SEQ ID NO 10
<211> LENGTH: 34
<212> TYPE: DNA
<213> ORGANISM: Artificial Sequence
<220> FEATURE:
<223> OTHER INFORMATION: PCR primer

<400> SEQUENCE: 10
tctgagctct gcatgctacg cccccaactg agag                                 34
```

PRODUCTION OF HETERO-OLIGOMERIC PROTEINS IN PLANTS

CROSS-REFERENCE TO RELATED APPLICATIONS

This application is the U.S. National Stage of International Application PCT/EP2006/000721 filed Jan. 27, 2006, which claims the benefit of U.S. Provisional Application No. 60/593,606 filed Jan. 28, 2005 and EP 05001819.1 filed Jan. 28, 2005; all of which are hereby incorporated herein in their entirety by reference.

FIELD OF THE INVENTION

The present invention relates to the production of hetero-oligomeric proteins in plant, plant parts or plant cell cultures using the plus-sense single stranded RNA viral vectors. The process and vectors described in the present invention provide plant cells with an increased yield of functional hetero-oligomeric recombinant protein, such as full-length antibody or hetero-oligomeric synthetic derivatives thereof including fusions with other proteins or their fragments.

BACKGROUND OF THE INVENTION

Plant-based molecular farming is an attractive opportunity for the production of recombinant proteins destined to be used in the field of human and animal health, preferably due to the potentially low production cost and attempts by biopharmaceutical industry to eliminate animal-derived proteins from manufacturing processes because of possible contamination of these products by human pathogens such as Bovine Spongiform Encephalopathy (BSE) or Creuzfeld-Jacob Disease (CJD, vCJD). However, high-yield production of hetero-oligomeric proteins in plant cells is a problem that cannot be resolved with the help of standard expression systems based on the use of strong constitutive or tissue-specific promoters for the following reasons: firstly, the majority of such recombinant proteins have a deleterious effect on plant growth and development, thus strongly compromising the yield; secondly, use of tissue-specific promoters (e.g. seed-specific) would require stable incorporation of genes encoding for pharmaceutical proteins into the genomes of edible crop plants (e.g. rice, corn, wheat), that might cause problems with transgene flow control in case of open field cultivation. Also, these systems are not commercially viable, if used in closed (greenhouse) environment due to the low yield of the product.

Plant virus-based transient expression systems (for review see: Porta & Lomonossoff, 1996, *Mol. Biotechnol.*, 5, 209-221; Yusibov et al. 1999, *Curr. Top. Microbiol. Immunol*, 240, 81-94; Gleba et al., 2004, *Curr. Opin. Plant Biol.*, 7, 182-188) are able to provide for high expression levels in plant leaf tissues and to some extent are capable to address the problems of cytotoxicity of recombinant proteins and their detrimental effect on plant development, as the technology allows to separate the growth and production stages. The best-established and commercially viable systems are based on plus-sense single-stranded RNA viral vectors, preferably on Tobacco Mosaic Virus (TMV)-derived vectors (Kumagai et al., 1994, *Proc. Natl. Acad. Sci. USA*, 90, 427-430; Mallory et al. 2002, *Nature Biotechnol.* 20, 622-625; U.S. Pat. No. 5,316,931; U.S. Pat. No. 5,589,367; U.S. Pat. No. 5,866,785; U.S. Pat. No. 5,977,438; WO02088369; WO02097080; WO0229068; U.S. Pat. No. 5,491,076). However these systems suffer from serious limitations that restrict their use to the production of simple, relatively small proteins. In part this is caused by the instability of viral vectors and the high frequency of their reversion to wild type, if they carry heterologous sequences larger than 1 kb. Also, serious limitation of the technology is the absence of viral vector systems capable of expressing complex hetero-oligomeric proteins like therapeutic monoclonal antibodies and their derivatives that represent the most valuable group of recombinant proteins.

There is only one publication addressing the expression of a full-length monoclonal antibody in plants using plant viral vectors (Verch et al., 1998, *J. Immunol. Meth.*, 220, 69-75). This paper describes the use of two systemic TMV-based viral vectors for the expression of heavy and light chains of monoclonal antibody in systemic leaves, whereby the different chains are expressed from different vectors upon co-infection of *N. benthamiana* plants with in vitro synthesised transcripts of said vectors. However, the yield of recombinant protein in said system is so low that the presence of assembled monoclonal antibody had to be confirmed with highly sensitive tests like Western blotting and ELISA. Due to the negligible yield of recombinant antibody, this system is not suitable for practical applications and has no commercial value. Since two or more TMV-based viral vectors are normally not present in the same plant tissues of an infected plant (see example 1), the detected antigen binding activity may be due to antibody that was in vitro assembled during the isolation procedure from heavy and light antibody chains expressed in separate cells or tissue. It was previously shown that functional antibodies can be assembled in vitro from denatured and reduced antibody components (Petersen & Dorrington, 1974, *J. Biol. Chem.*, 17, 5633-5641; Maeda et al. 1996, *Protein Engineering*, 9, 95-100). However, the efficiency of such assembly in the absence of conditions favourable for such an assembly is very low.

Therefore, there is no large-scale expression system for recombinant hetero-oligomeric proteins in plants, the yield and efficiency of which would be sufficient to compete on the market with other large-scale expression systems like fungal or insect cell expression systems. Such a plant expression would have to fulfil the following criteria as good as possible:
(i) high yield, including expression of the hetero-oligomeric protein of interest in as many plant tissues as possible and in as many cells of said tissues;
(ii) for preventing a deleterious effect of recombinant protein expression on plant growth, expression of the protein or product of interest should be transient (or switchable) such that expression can be started at a desired stage of plant development;
(iii) to provide for an optimal ratio of polyproteins encoding for different subunits of hetero-oligomeric protein in plant cell, thus supporting for high yield of recombinant protein at the level of said recombinant protein assembly from said subunits.

Therefore, it is an object of this invention to provide an efficient process of producing a hetero-oligomeric protein in a plant, plant part, or plant cell culture. A further object is the provision of a high-yield plant expression system capable of expressing hetero-oligomeric protein. It is another object of the invention to provide an efficient process of co-expressing more than one polypeptide of interest in the same plant cell. Further, it is an object of the invention to provide a fast and high-yield method for expressing antibodies in a plant, plant part or plant cell culture.

GENERAL DESCRIPTION OF THE INVENTION

The invention provides a process of producing in a plant, in plant tissue, or in plant cells a hetero-oligomeric protein comprising at least a first and a second protein subunit, said process comprising expressing in plant cells at least said first and said second protein subunit by
(i) providing to said plant, said plant tissue or said plant cells a first and a second plus-sense single-stranded RNA viral vector, said first viral vector encoding at least said first protein subunit, said second viral vector encoding at least said second protein subunit, whereby at least said first viral vector and said second viral vector are non-competing viral vectors; or
(ii) providing to said plant, said plant tissue or said plant cells a plus-sense single-stranded RNA viral vector encoding at least said first and said second protein subunit.

In one embodiment, said first viral vector and said second viral vector are non-competing in that they are different viral vectors. In another embodiment, said first viral vector and said second viral vector are non-competing in that they are not derived from the same RNA virus. In another embodiment, said first viral vector and said second viral vector are non-competing in that they differ in a sequence portion other than sequence portions coding for said first and second protein subunits. In another embodiment, said first viral vector and said second viral vector are non-competing in that they are derived from RNA viruses belonging to different virus species. In another embodiment, said first viral vector and said second viral vector are non-competing in that they are derived from RNA viruses belonging to different virus genera.

Another embodiment of the invention is a process of producing in a plant, in plant tissue, or in plant cells an antibody comprising at least a first and a second protein subunit like a heavy and a light antibody chain, said process comprising expressing in plant cells at least said first and said second protein subunit by
(i) providing to said plant, said plant tissue or said plant cells by *Agrobacterium*-mediated transfection a DNA precursor of a first plus-sense single-stranded RNA viral vector and a DNA precursor of a second plus-sense single-stranded RNA viral vector, said first viral vector encoding at least said first protein subunit, said second viral vector encoding at least said second protein subunit, whereby at least said first viral vector or said second viral vector lack an open reading frame coding for a functional protein necessary for systemic movement of said first or said second viral vector in said plant; or
(ii) providing to said plant, said plant tissue or said plant cells by *Agrobacterium*-mediated transfection a DNA precursor of a plus-sense single-stranded RNA viral vector encoding at least said first and said second protein subunit, whereby said viral vector lacks an ORF coding for a functional protein necessary for systemic movement.

The invention further provides a process of producing in a plant, in plant tissue or in plant cells a hetero-oligomeric protein comprising at least a first and a second protein subunit, said process comprising expressing in plant cells at least said first and said second protein subunit from one or more plus-sense single-stranded RNA viral vector(s).

Further embodiments of the invention are described in the claims and the following description.

The inventors of the present invention have surprisingly identified ways of producing hetero-oligomeric proteins with high yield in plants using plant viral vectors. Efficient production of hetero-oligomeric proteins in plants requires high-yield production of the different protein subunits of the hetero-oligomeric protein in the same plant cells. In this way, the hetero-oligomeric protein can be efficiently assembled in cells having expressed said at least two protein subunits using natural protein assembling capabilities of said cells like those of the endoplasmatic reticulum (ER). Inefficient in vitro assembly of said hetero-oligomeric protein is therefore not necessary. The present invention achieves for the first time efficient co-expression of two or more proteins in the same cells by the above step (i) or by the above step (ii) or by a combination of the above steps (i) and (ii).

Said first protein subunit is encoded in the RNA viral vector by a first heterologous (nucleic acid) sequence. Said second protein subunit is encoded in the viral vector by a second heterologous (nucleic acid) sequence. These heterologous sequences are thus RNA sequences of said viral vector(s) and typically comprise or encode regulatory sequences required for expressing said protein subunits. Examples of such regulatory sequences are subgenomic promoters, IRES elements, and 3'-untranslated sequences. Herein, a sequence is a heterologous sequence if it does not naturally occur in the virus from which said viral vector(s) is/are derived.

The hetero-oligomeric protein producible according to the present invention has at least a first and a second subunit, whereby said first and said second subunits have different polypeptide sequences. Thus, said first and said second subunit typically have to be expressed from different heterologous nucleic acid sequences. The subunits of an oligomeric protein assemble to form the quaternary structure of the oligomeric protein. Assembly of the subunits typically involves non-covalent bonds between the subunits. Additionally, covalent bonds may be formed between said protein subunits, e.g. disulfide bonds.

In one embodiment, said hetero-oligomeric protein is a hetero-dimeric protein, i.e. a protein having two different protein subunits. In another embodiment, said hetero-oligomeric protein may have more than two different subunits e.g. 3 or 4 different subunits (hetero-trimeric or hetero-tetrameric protein, respectively). In a further embodiment, said hetero-oligomeric protein may have two different subunits, whereby one or both of said subunits may be present in said hetero-oligomeric protein more than one time. Examples of the subunit organization of said hetero-oligomeric protein are $A_aB_b$, $A_aB_bC_c$, and $A_aB_bC_cD_d$, wherein A stands for a first protein subunit, B stand for a second protein subunit, and C and D stand for further protein subunits. Each capital letter A, B, C, and D stands for protein subunits different from the other protein subunits and small letters stand for integers of at least 1 that indicate the number of copies of the respective protein subunit in said hetero-oligomeric protein. An example are IgG antibodies which have the subunit organization $A_2B_2$, wherein A represents a first protein subunit (e.g. the heavy chain) and B represents a second protein subunit (e.g. the light chain). Preferably, the hetero-oligomeric protein produced according to the invention has two or three different protein subunits, more preferably it has two different protein subunits.

In the process of the invention, at least said first and said second protein subunits are expressed in cells of said plant, of said plant tissue, or of said plant cells by said step (i) or/and said step (ii). Each of said steps (i) and (ii) allows expression of at least said first and said second protein subunit in the same cells such that said hetero-oligomeric protein can be produced efficiently in said cells. Steps (i) and (ii) can be performed in parallel, notably for the production of hetero-oligomeric proteins having three, four, or more different protein subunits (see example 7).

Said plus-sense single-stranded RNA viral vector(s) of the invention are also referred to herein simply as "viral vector". Typically, said plus-sense single-stranded RNA viral vectors are derived from plus-sense single-stranded plant RNA viruses.

In step (ii), said plant, said plant tissue or said plant cells is/are provided with a plus-sense single-stranded RNA viral vector encoding at least said first and said second protein subunit. Said viral vector encoding at least said first and said second protein subunit contains, as an insert, a first heterologous sequence encoding said first protein subunit expression of which may be under the control of a first sub-genomic promoter. Further, said viral vector contains, as an insert, a second heterologous sequence encoding said second protein subunit expression of which may be under the control of a second sub-genomic promoter. If both said first and said second protein subunits are expressed under the control of a subgenomic promoter, these subgenomic promoters preferably differ in sequence for avoiding self-homology in said viral vector, which could lead to undesired recombination events in plant cells. Such different subgenomic promoters may be taken from different strains or species of a plant virus, e.g. one subgenomic promoter may be (or may be derived from) the coat protein (CP) subgenomic promoter of tobacco mosaic virus (TMV) U1 and the other subgenomic promoter may be (or may be derived from) the CP subgenomic promoter of TMV U5 or from crucifer-infecting tobamovirus (cr-TMV).

Instead of said first or said second subgenomic promoter, translation of said first or said second protein subunit may be under control of an IRES (internal ribosome entry site) element. Although translation of both said first and said second protein subunits may be under the control of IRES elements, it is preferred that at least one of said protein subunits is expressed using a subgenomic promoter. The IRES elements for use in the present invention may be taken from plant viruses like cr-TMV or other plant viruses (Proc Natl Acad Sci USA 2002, 99, 5301-6; Virology 1999, 263, 139-54; WO03020927; WO0229068).

Said viral vector of step (ii) is preferably incapable of systemic movement in said plant or said plant tissue. This can be achieved e.g. by omitting a functional origin of viral particle assembly. In tobamoviruses for example, the origin of viral particle assembly is located in the MP ORF. Thus the origin of viral particle assembly can be omitted by deleting fully or partly the MP ORF from said viral vector. Said viral vector is thus preferably devoid of a functional movement protein (MP) ORF. More preferably, said viral vector is devoid of a functional protein necessary for systemic movement of said viral vector. In this embodiment, said viral vector may be devoid of a functional coat protein ORF, and most preferably said viral vector is devoid of both a functional movement protein ORF and a functional coat protein ORF. Omitting an MP ORF and/or a CP ORF from the viral vector provides more space for encoding at least said first and said second protein subunit in said viral vector without compromising viral vector stability. In this embodiment, said viral vector is preferably provided to many cells of said plant or said plant tissue for achieving infection of many cells. This may best be achieved by providing a DNA precursor of said RNA viral vector as T-DNA using *Agrobacterium* (see below).

The virus said viral vector for step (ii) is derived from may be any plus-sense single-stranded plant RNA virus, e.g. those listed in chapter "Detailed Description". Preferred groups of viruses are tobamoviruses, potexviruses, and potyviruses. Most preferred viruses are TMV and PVX. Said viral vector will at least contain the ORFs from the virus it is derived from that encode proteins required for replication of said viral vector. Said viral vector typically further contains regulatory elements for viral replication and at least one subgenomic promoter.

In step (i), said plant, said plant tissue or said plant cells are provided with a first and a second plus-sense single-stranded RNA viral vector. Said first viral vector encodes at least said first protein subunit, said second viral vector encodes at least said second protein subunit.

Step (i) allows to produce hetero-oligomeric proteins having two different protein subunits. Step (i) also allows to produce hetero-oligomeric proteins having more than two different subunits, e.g. three or four different protein subunits. In this case, said plant, plant tissue or plant cells may be provided with a first, a second, and a third viral vector (and optionally with a further viral vector), each encoding one of said different protein subunits. If three or four different protein subunits have to be expressed in step (i), the respective three or four viral vectors are preferably all non-competing viral vectors with each other. In the case of three viral vectors, the first viral vector may be derived from a tobamovirus, the second viral vector may be derived from a potyvirus, and the third viral vector may be derived from a potexvirus.

Two viral vectors are non-competing if they can express efficiently the protein subunits they encode in the same plant cell (co-expression). Co-expression requires that the at least two different viral vectors do not outcompete each other during replication before having expressed substantial amounts of the heterologous sequences they encode. The higher the sequence differences on the RNA level of said at least two viral vectors, the more they are non-competing in the same plant cells. Said first viral vector and said second viral vector are non-competing viral vectors, since said first viral vector and said second viral vector are different viral vectors.

For being non-competing, said first and said second viral vectors (said two non-competing viral vectors) differ, in one general embodiment, at least in a sequence portion other than said heterologous sequences coding for said protein subunits. Preferably, such a difference in a sequence portion other than said heterologous sequences is a sequence portion derived from a plant RNA virus such as a sequence portion involved in a viral function such as viral replication in plant cells (e.g. a sequence coding for a replicase), translation of a viral protein (e.g. a subgenomic promoter) or viral cell-to-cell or long distance movement.

For being non-competing, said first and said second viral vectors (said two non-competing viral vectors) are, in another general embodiment, derived from different plant viruses. In one example of this embodiment, said at least two non-competing viral vectors are not derived from viruses of the same virus strain. In another example, said at least two non-competing viral vectors are not derived from viruses of the same virus species. In a further example, said at least two non-competing viral vectors are not derived from viruses of the same virus genus. Thus, said first viral vector and said second viral vector are preferably derived from viruses of different strains, more preferably from viruses of different species, most preferably from viruses of different genera.

Said first viral vector may be derived from a virus belonging to the genus Potexvirus and said second viral vector may be derived from a virus belonging to the genus Potyvirus. Specifically, said first viral vector may be derived from Potato Virus X and said second viral vector may be derived from Potato Virus Y.

In case of a potyviral vector, said protein subunit can be expressed as a fusion with a viral polyprotein, whereby a protein subunit of the invention can be separated from said polyprotein by a potyviral protease recognition site.

In another embodiment, said first viral vector may be derived from a virus belonging to the genus Potexvirus and said second viral vector may be derived from a virus belonging to the genus Tobamovirus. Specifically, said first viral vector may be derived from Potato Virus X and said second viral vector may be derived from Tobacco Mosaic Virus.

"Being derived from a virus" means that the viral vector contains genetic elements or sequence portions from the virus it is derived from. In one embodiment, said viral vector(s) contain(s) a replicase ORF (open reading frame) taken from an RNA virus. In another embodiment, a viral vector contains a movement protein ORF from an RNA virus and, optionally, also a replicase ORF. Viral genetic elements taken from an RNA virus may, if desired, be mutated e.g. for introducing the restriction sites required for cloning of the viral vector.

An embodiment wherein said first viral vector and said second viral vector are both based on tobacco mosaic viral vector TMV 30 B is excluded from step (i) of the process of the invention, since in this case said first viral vector and said second viral vector are not different viral vectors but are the same viral vectors (cf. Verch et al., J. Immunological Methods 220 (1998) 69-75).

Said first and said second viral vectors (said non-competing viral vectors) preferably have a sequence homology on RNA level of at most 90%, more preferably of at most 80%, even more preferably of at most 70%, and most preferably of at most 60%. More specifically, any sequence segment of said first viral vector of 100 bases preferably has a sequence homology to any sequence segment of 100 bases of said second viral vector of at most 90%, preferably at most 80%, more preferably at most 70%, and most preferably of at most 60%.

In one embodiment, the replicase ORF (or ORFs if the replicase is encoded by more than one ORF) of said first viral vector and the replicase ORF (or ORFs if the replicase is encoded by more than one ORF) of said second viral vector have a homology of at most 90%, more preferably of at most 80%, even more preferably of at most 70%, and most preferably of at most 60%. In another embodiment, the replicase ORF of said first viral vector and the replicase ORF of said second viral vector have an identity of at most 85%, more preferably of at most 75%, even more preferably of at most 65%, and most preferably of at most 55%.

In step (i), said first viral vector preferably contains a first heterologous sequence encoding said first protein subunit expression of which may be under the control of a first subgenomic promoter. Said second viral vector contains a second heterologous sequence encoding said second protein subunit expression of which may be under the control of a second subgenomic promoter. One or both of said subgenomic promoters may be replaced by an IRES element. Similar as described above for step (ii), if both said first and said second protein subunits are expressed under the control of a subgenomic promoter, these subgenomic promoters preferably differ in sequence for avoiding homology between said first and said second (and any further viral vector) viral vector, which could lead to undesired recombination events in plant cells. Such different subgenomic promoters may be taken from different strains or species of plant virus, e.g. one subgenomic promoter may the coat protein (CP) subgenomic promoter of tobacco mosaic virus (TMV) U1 and the other subgenomic promoter may be the CP subgenomic promoter of TMV U5 or from crucifer-infecting tobamovirus (cr-TMV).

Since ORFs of plant viruses that are required for cell-to-cell or long distance movement may be omitted upon constructing the viral vectors of the invention, the relatedness of said non-competing viral vectors may be determined by comparing the replicase ORFs of said viral vectors.

Said first and said second heterologous sequences encoding said first and said second protein subunit, respectively, may be added as an additional sequence to said viral vectors. Said heterologous sequences are preferably added such that high level expression is achieved. For this purpose, said heterologous sequence is added at the 3' end of the virus, since the 3' ORF is frequently the ORF that is expressed at the highest level in many viruses. Preferably, however, said heterologous sequences replace a sequence native to said virus, e.g. the natural 3' ORF of said virus which is the CP ORF in many viruses like tobamoviruses. Thus, said first and/or said second viral vector preferably lacks an ORF for systemic movement of said viral vector. Said viral vectors may further lack an ORF for cell-to-cell movement like the MP ORF in tobamoviruses.

In this invention, step (i) and step (ii) may be combined, notably for expressing three or more different subunits of a hetero-oligomeric protein. If a hetero-oligomeric protein having four different protein subunits is to be produced, two protein subunits may be expressed according to step (i) and two further protein subunits may be produced in the cells of a plant or plant tissue according to step (ii). Preferably, however, two protein subunits may be expressed from a first viral vector and two protein subunits may be expressed from a second viral vector that is non-competing to the first viral vector. If a hetero-oligomeric protein having three different protein subunits is to be produced, said three protein subunits may be expressed according to step (i) by expressing two proteins from a first viral vector similarly as described for step (ii) and expressing a third protein subunit from a non-competing viral vector.

The viral vectors of the invention are typically engineered on DNA level. If said viral vectors are provided to cells of a plant or to cells of plant tissue as RNA viral vectors, said DNA may be transcribed in vitro to said RNA viral vectors e.g. using a bacteriophage polymerase like T7 polymerase together with a suitable promoter. Two different viral vectors are preferably applied to said plant as a mixture for ensuring that cells of said plant are provided with both viral vectors. Preferably, however, the viral vectors of the invention are provided to cells of a plant or to cells of plant tissue by transforming said plant or said plant tissue with DNA precursors of said RNA viral vectors. Said DNA precursors have a transcriptional promoter active in cells of said plant for forming said viral vectors by transcription of said DNA precursors. Most preferably, said DNA precursors are T-DNA in Agrobacterial Ti plasmids. Two or more viral vectors may then be provided to said plant or said plant tissue by treating said plant with a mixture (e.g. a suspension) of two or more *Agrobacterium* strains, whereby each strain contains a T-DNA encoding a particular viral vector. Treating substantial parts of a plant with such an *Agrobacterium* suspension may replace the systemic movement function and/or the cell-to-cell movement function of natural plant viruses.

Transient transfection of said plant, plant tissue or plant cells with DNA precursors of said viral vectors by way of *Agrobacterium* is most preferred in the present invention. However, said DNA precursors of said viral vectors may be stably incorporated into plant chromosomal DNA. Release of said viral vector(s) from chromosomal DNA may be controlled by inducible promoters.

If said viral vectors are provided to said plant by way of DNA precursors, it is preferred that measures are taken for improving the efficiency of transfer of said viral vectors from the cell nuclei where they are transcribed to the cytoplasm where said viral vectors replicate. This may be achieved by including introns in said DNA precursors, notably in the replicase ORFs of the viral vectors as described in detail in International patent application PCT/EP05/000492, published as WO2005/71090, that is incorporated herein by reference.

The process of the invention may be applied to any plant for which plant viral expression systems exist or will be worked out in the future. Said plant may be a monocot or a dicot. Among dicots, Solanaceae, Brassicaceae, Chenopodiaceae, and Legume are preferred. Among Solanaceae, the genus *Nicotiana* like *N. tabacum* or *N. benthamiana* is preferred. Other preferred plants are *Medicago sativa* and *Beta* species like *Beta vulgaris*.

The process of the invention is used for producing hetero-oligomeric proteins in plant systems. Preferred hetero-oligomeric proteins are immunoglobulins like immunoglobulins of the following classes: immunoglobulin G, immunoglobulin A, immunoglobulin M, immunoglobulin D, and immunoglobulin E. These immunoglobulins may comprise at least a portion of an antigen binding domain. As the case requires, these immunoglobulins produced according to the invention may be modified relative to native animal immunoglobulins, provided they comprise at least two different protein subunits. The immunoglobulin may comprises a protection protein in association with an immunoglobulin heavy chain, wherein the protection protein comprises a portion of a polyimmunoglobulin receptor. Another preferred hetero-oligomeric protein is insulin.

The hetero-oligomeric protein of the invention may be modified in many different ways relative to the native protein as the case requires. In the hetero-oligomeric protein, a native leader sequence forming a secretion signal of one or more protein subunits of the native hetero-oligomeric protein may be replaced by plant-specific signal peptides. Said plant-specific signal peptides may be derived from tobacco calreticulin and/or rice alpha-amylase. At least one or at least two or more subunits of said hetero-oligomeric protein may contain an endoplasmatic reticulum retention signal KDEL for improving assembly of said hetero-oligomeric protein from said subunits in plant cells. Further, said heterologous sequences encoding said protein subunits may be mutated in order to partially or completely remove glycosylation sites from said hetero-oligomeric protein. Moreover, the glycosylation pattern of the hetero-oligomeric protein to be expressed may be changed e.g. by engineering a component of the plant glycosylation machinery like one or more glycosyl transferases.

The hetero-oligomeric protein of the invention may be isolated from the plant, plant tissue or plant cells after expression according to generally known procedures. Said hetero-oligomeric protein may then be purified to substantial homogeneity, which state may be defined such that bands due to said hetero-oligomeric protein on a coomassie-staned SDS-PAGE account for at least 70%, preferably at least 80%, and most preferably at least 90% of the staining of a lane as determined by a conventional gel reader.

(B) is a schematic representation of T-DNA regions of pICH17272 and pICH18505. P—transcription promoter; T—transcription termination region; RdRP viral RNA-dependent RNA polymerase; MP—viral movement protein; 3'NTR—viral 3' non-translated region; Cr-sgp—CP subgenomic promoter region of crTMV strain; GOI—gene of interest.

(C) are a schematic representations of restriction maps of the T-DNA regions of pICH17272 and pICH18505.

Figure 2:
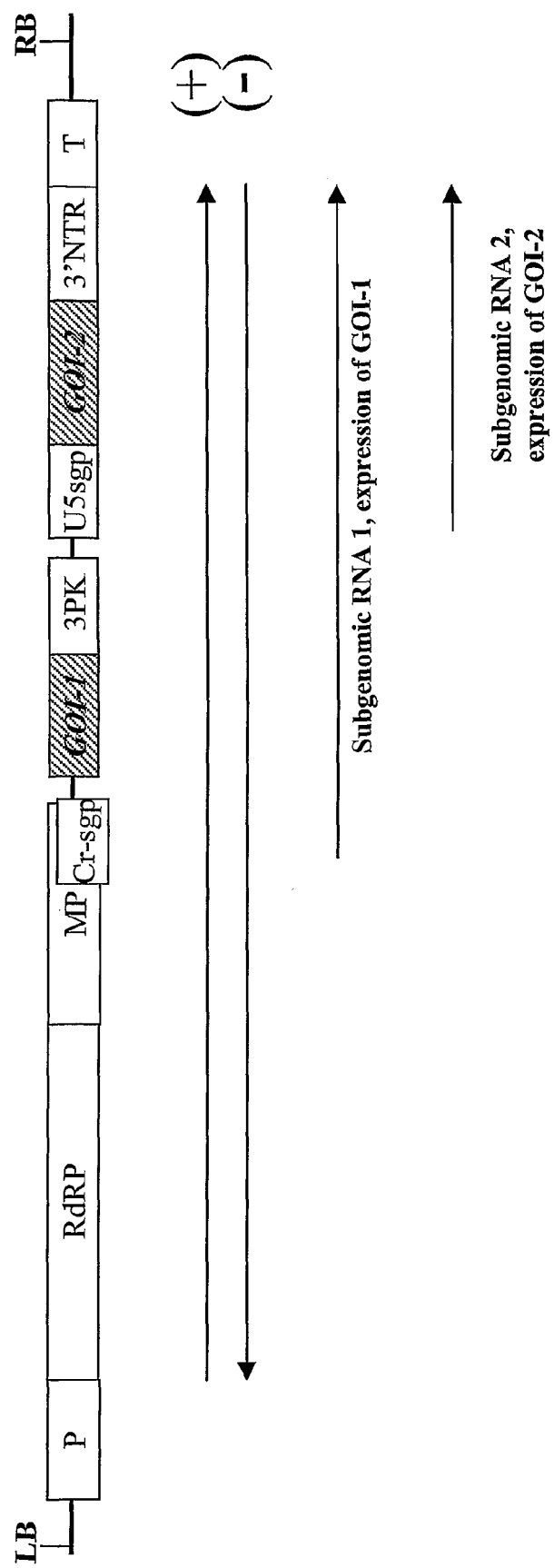

FIG. 2 depicts a schematic representation of a T-DNA region of a viral vector designed for co-expression of two different transgenes (GOI-1 and GOI-2) from different subgenomic promoters. P—transcription promoter; T—transcription termination region; RdRP viral RNA-dependent RNA polymerase; MP—viral movement protein; 3'NTR—viral 3' non-translated region; Cr-sgp—CP subgenomic promoter region of crTMV strain; 3PK—triple pseudo knot region; U5sgp—CP subgenomic promoter of TMV-U5 strain. GOI—gene of interest.

Figure 3A:
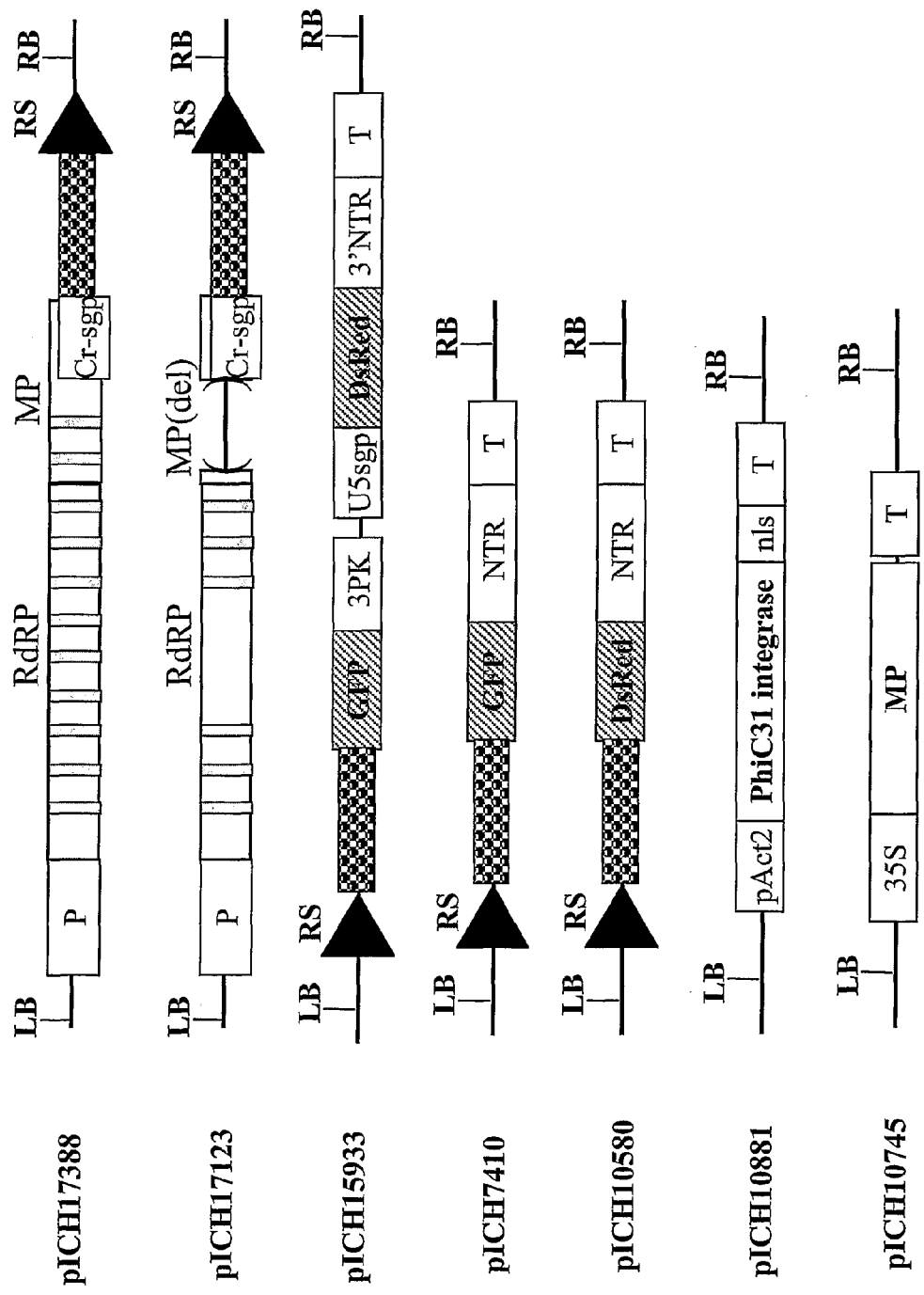
Figure 3B:
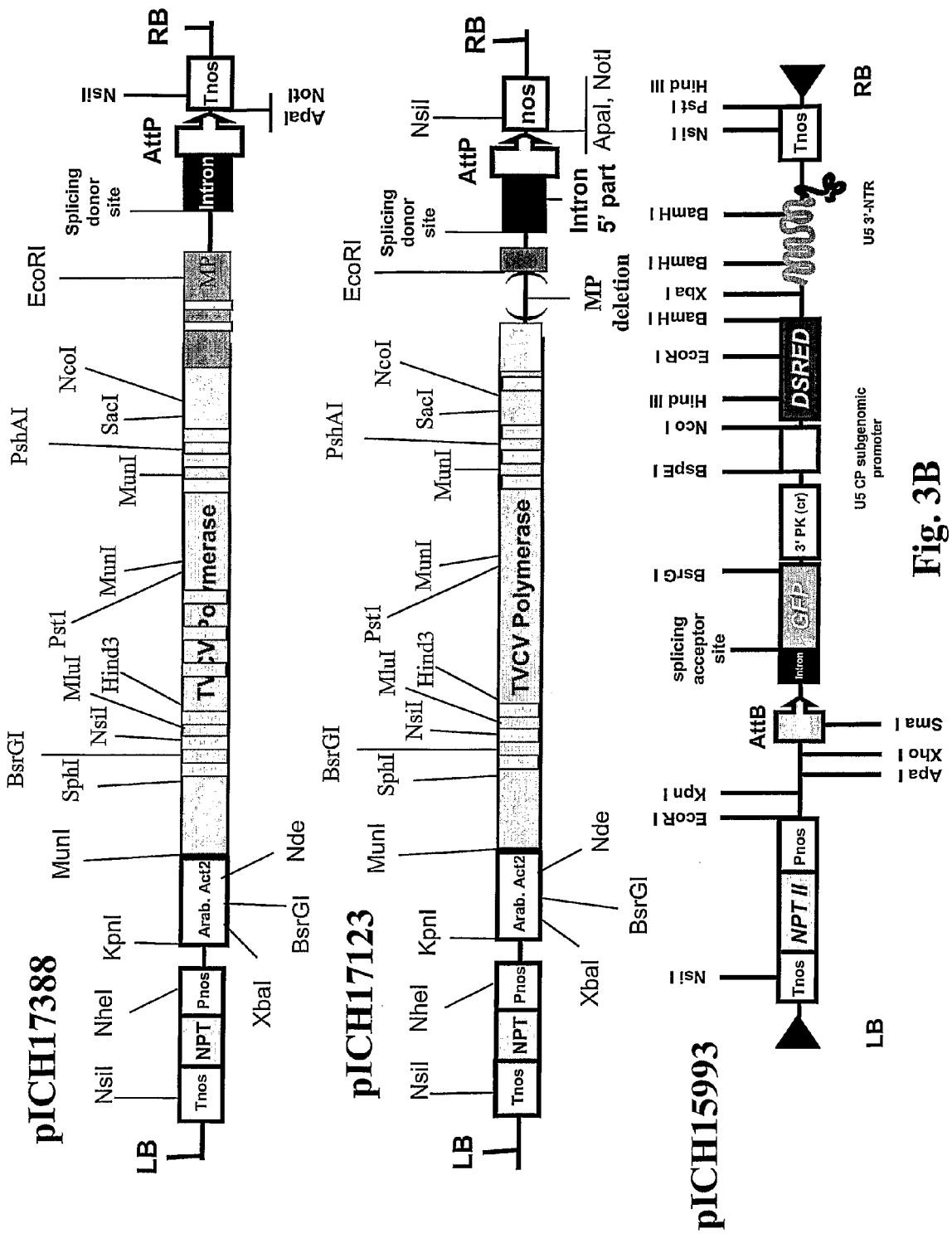
Figure 3C:
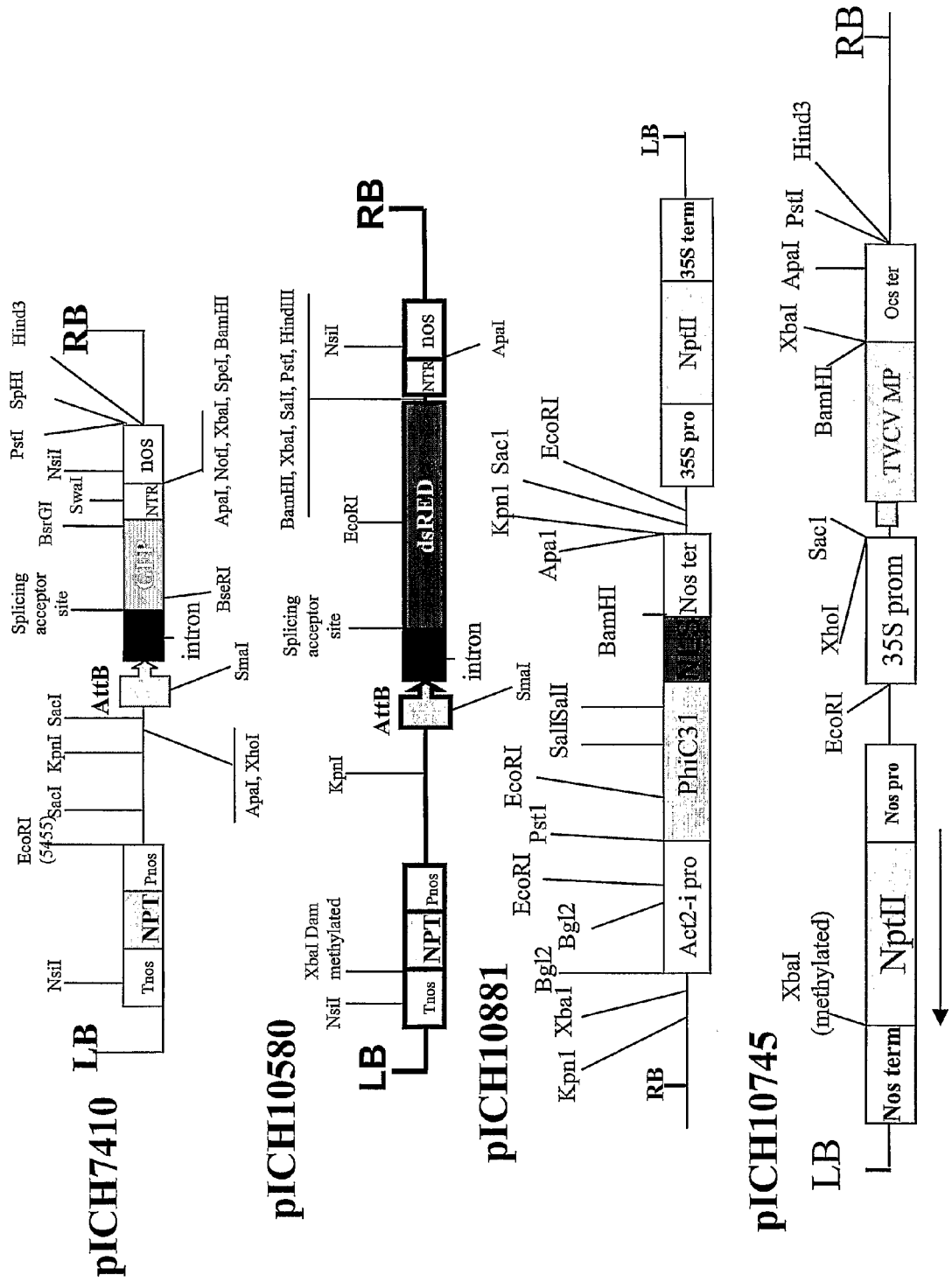

FIG. 3 (A) depicts schematic representations of T-DNA regions of constructs pICH17388, pICH17123, pICH15933, pICH7410, pICH10580, pICH10881 and pICH10745. RS—recombination site recognised by PhiC31 integrase. Grey vertical bars indicate introns.

(B) depicts restriction maps of the T-DNA regions of pICH17388, pICH17123, pICH15933.

(C) depicts restriction maps of the T-DNA regions of pICH7410, pICH10580, pICH10881 and pICH10745.

Figure 4:
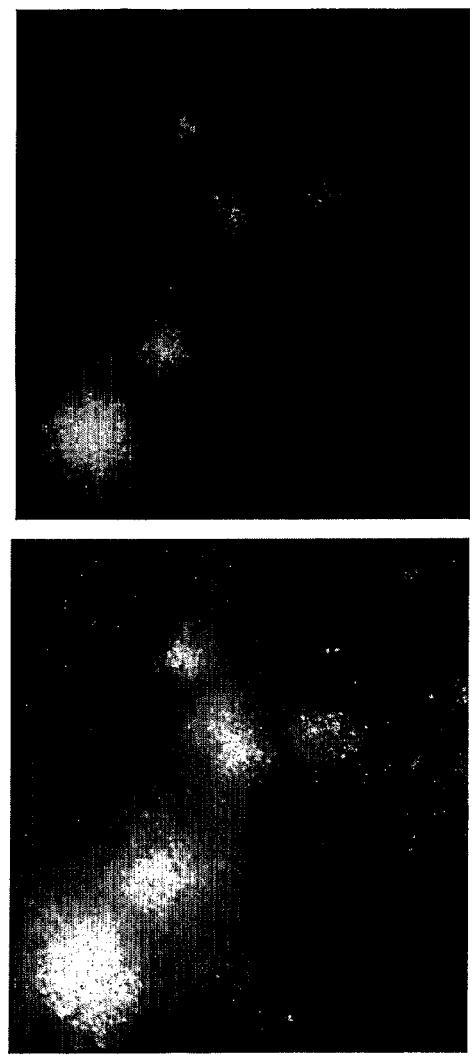
Figure 4:
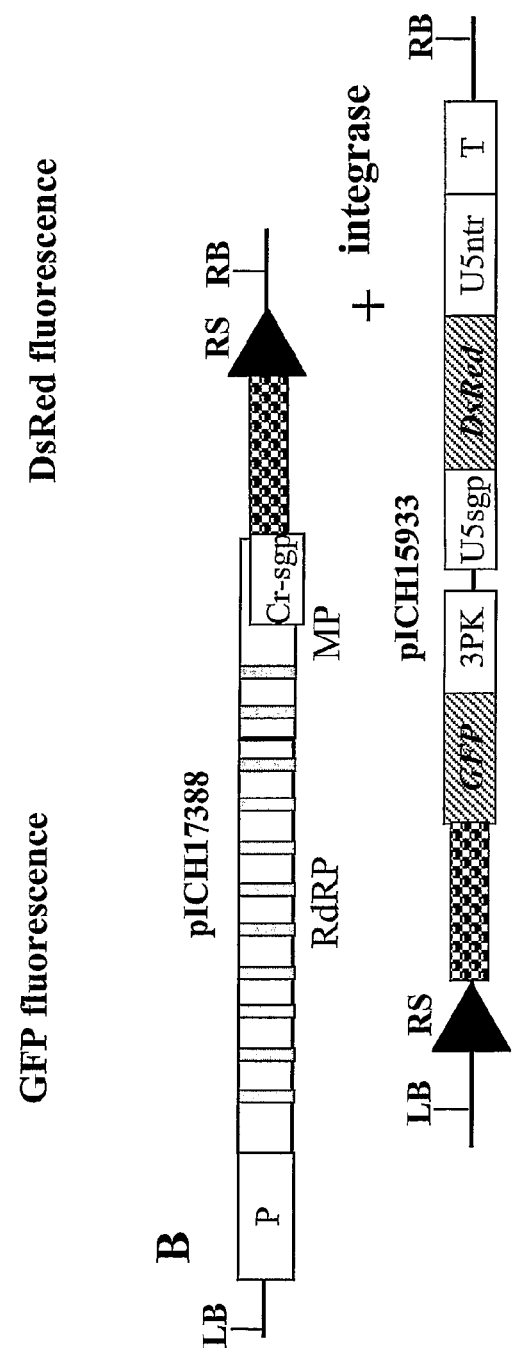

FIG. 4 shows in (A) fluorescence microscope micrographs of an *N. benthamiana* leaf region 6 days after agrobacterial delivery of DNA precursors pICH17388 and pICH15933 together with a recombinase source. RS—recombination site recognised by PhiC31 integrase.

Figure 5:
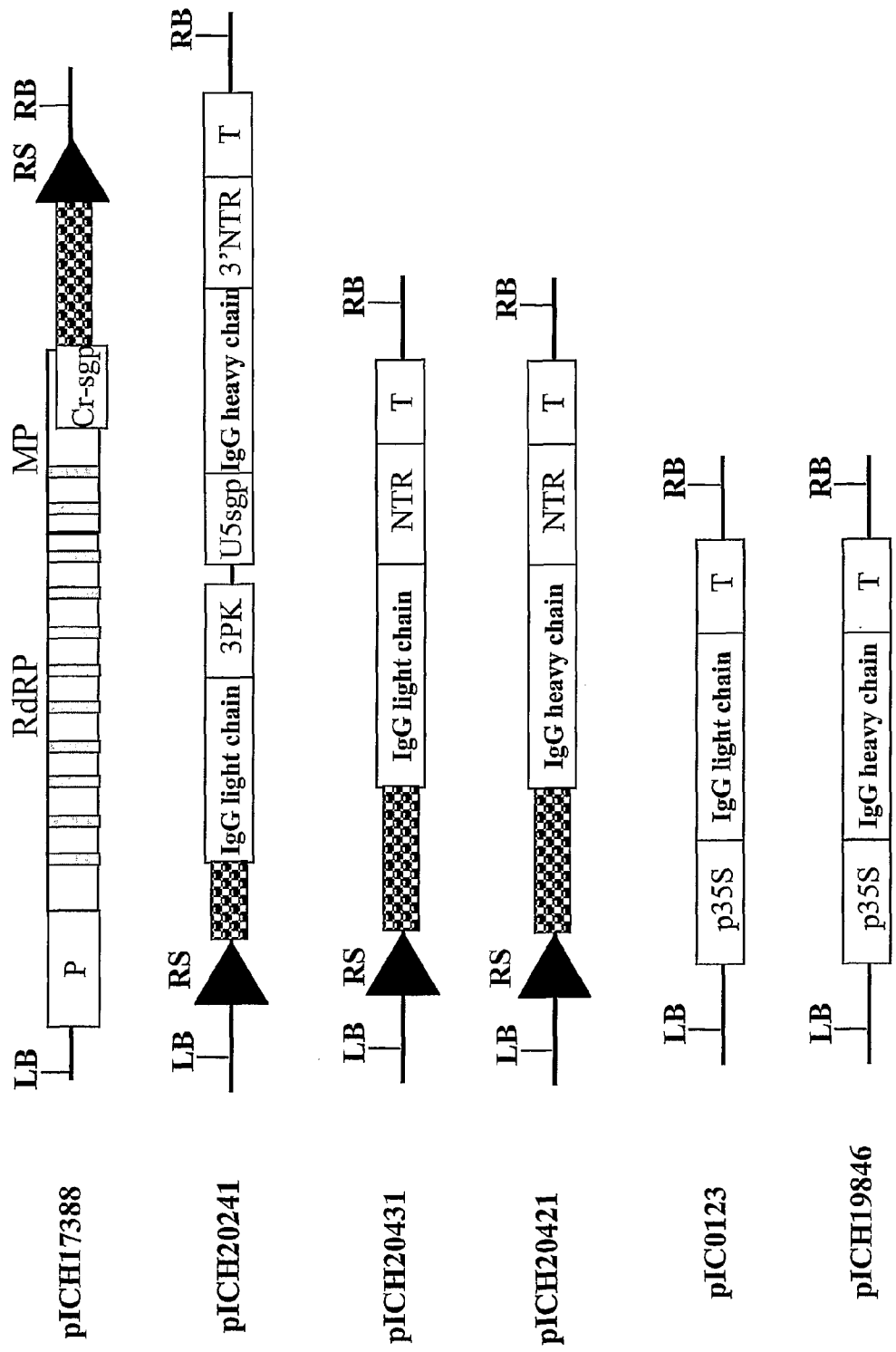

FIG. 5 depicts schematic representations of T-DNA regions of different vector systems for the expression of heavy and light chains of an antibody. RS—recombination site recognised by PhiC31 integrase.

Figure 6:
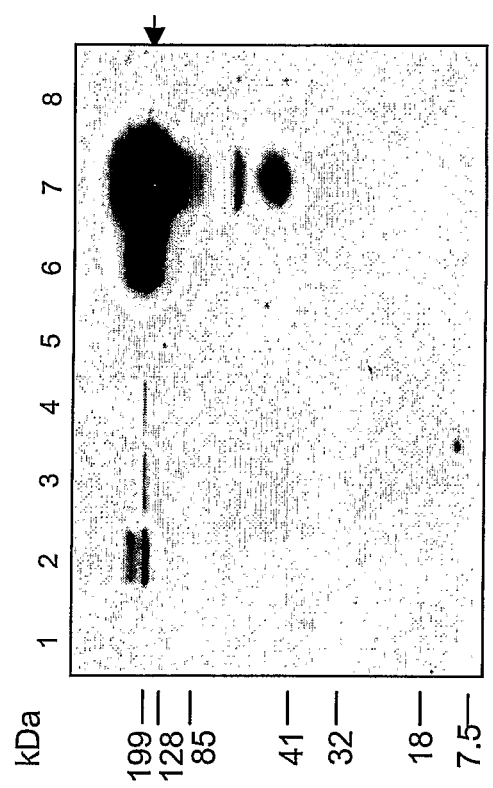

FIG. 6 shows a Western blot of the expression of an IgG in *Nicotiana benthamiana* leaves using viral provector system. Electrophoretic separation of TSP was carried out on a 12% gel under non-reducing conditions. Detection of expressed protein was performed with anti-human IgG fraction from rabbit conjugated with HRP (Sigma) diluted $6\times10^3$.

Lane: 1—uninfected leaf tissue; lane 2—IgG heavy chain expressed in cytosol (pICH17388);

lane 3—IgG heavy and light chains, co-expression with 35S promoter constructs (pIC0123+pICH19846); lane 4—the same as lane 3 with P19 (pICH6692);

lane 5—GFP expressed with 35S promoter constructs and P19 (pICH5290+pICH6692);

lane 6—IgG heavy and light chains co-expression with bicistronic construct pICH19860;

lane 7—IgG heavy and light chains co-expression with bicistronic construct pICH19860 (MP deficient 5' pro-vector pICH17123, MP in trans pICH10745);

lane 8—GFP and dsRED co-expressed in cytosol, MP provided in trans (pICH17123+pICH19919+pICH10745).

Figure 7:
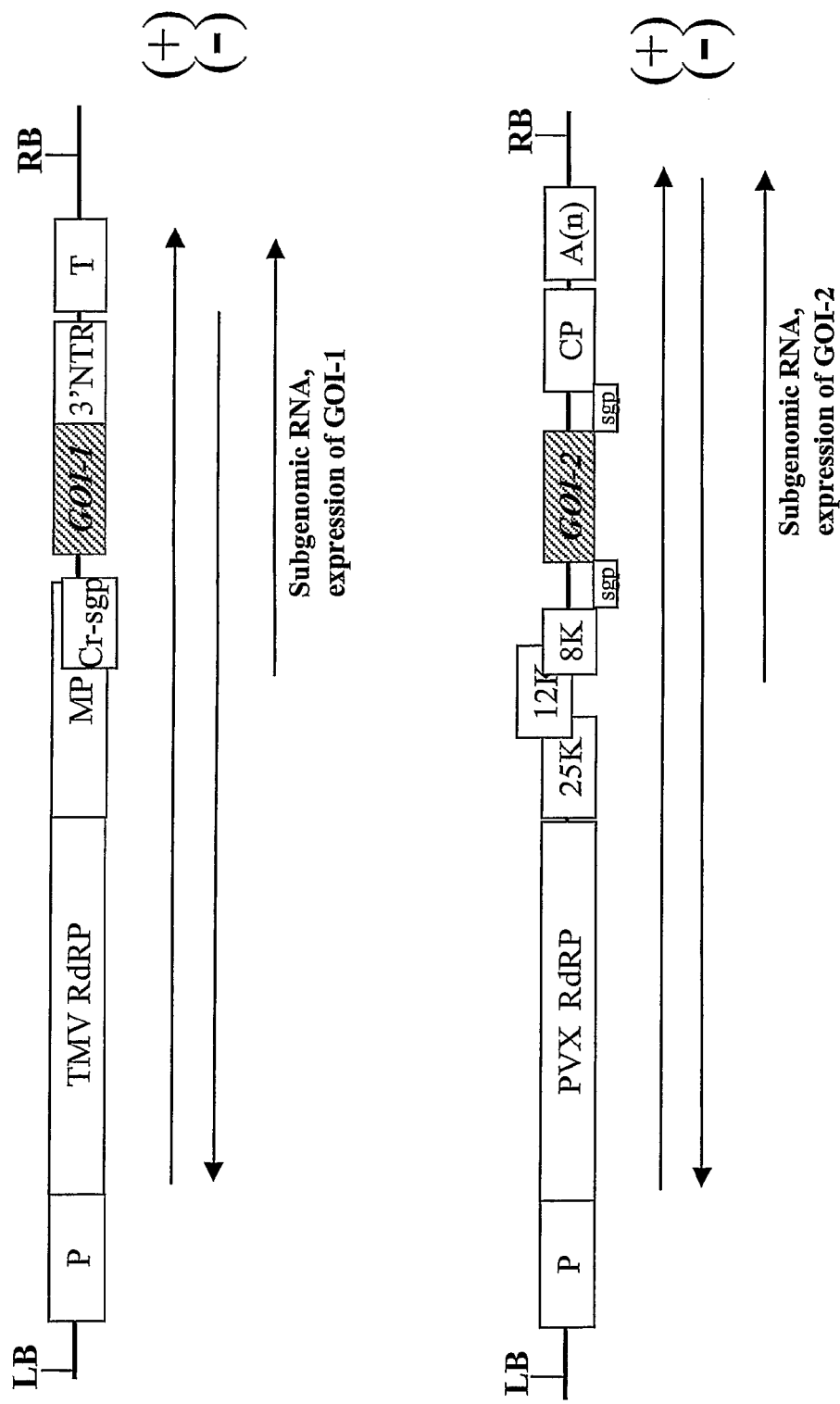

FIG. 7 depicts a schematic representations of T-DNA regions encoding non-competing viral vectors designed for co-expression of different protein subunits of interest in the same plant cell. P—transcription promoter; T—transcription termination region; TMV RdRP viral RNA-dependent RNA polymerase of Tobacco Mosaic Virus; PVX RdRP viral RNA-dependent RNA polymerase of Potato Virus X; MP—viral movement protein; 3'NTR—viral 3' non-translated region; Cr-sgp—CP subgenomic promoter region of crTMV strain; GOI—gene of interest coding for a protein subunit of interest.

Figure 8:
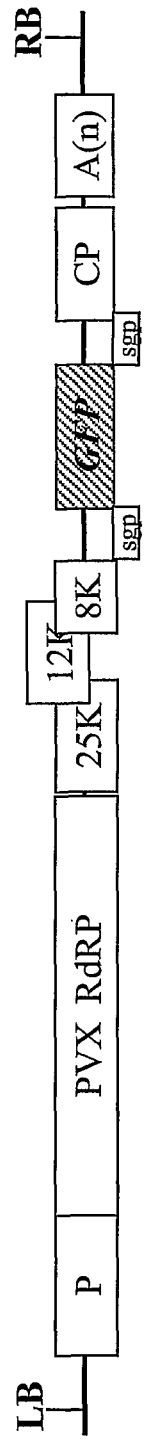

FIG. 8 depicts a schematic representation of the T-DNA region of binary vector pIC0130.

Figure 9:
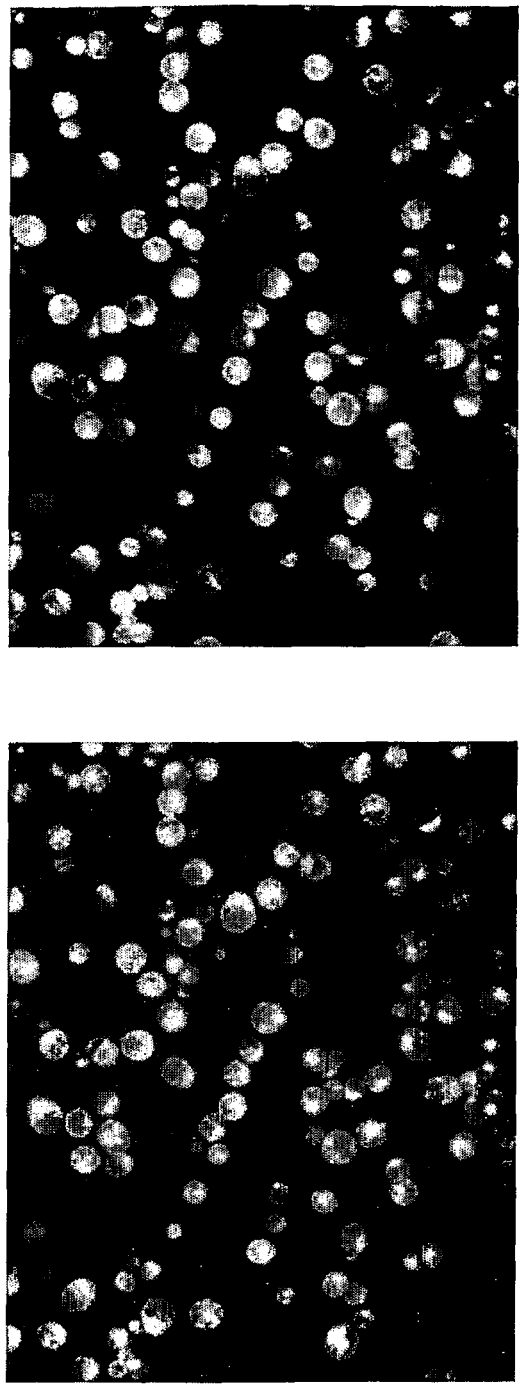

FIG. 9 shows co-expression of GFP and dsRED in plant cells using TMV (pICH17388+pICH10580) and PVX-based (pIC0130) vectors: visualisation of GFP and dsRED in protoplast isolated from agroinoculated N. benthamiana leaves.

FIG. 10 (A) depicts schematic representation of the T-DNA regions of binary vectors pICH17620, pICH20431, pICH21240, pICH20421, and pICH21370.

(B) is a schematic representation of the T-DNA regions of binary vectors pICH11599, pICH21910 and pICH21920.

(C) is a schematic representation of the T-DNA regions of binary vectors pICH21282, pICH10990, pICH22250 and pICH22240. Lv and Lc—variable and conservative regions of light chain; Hv and Hc—variable and conservative regions of heavy chain.

(D) is a schematic representation of cloning scheme for PVX-derived provector pICH21380.

Figure 11A:
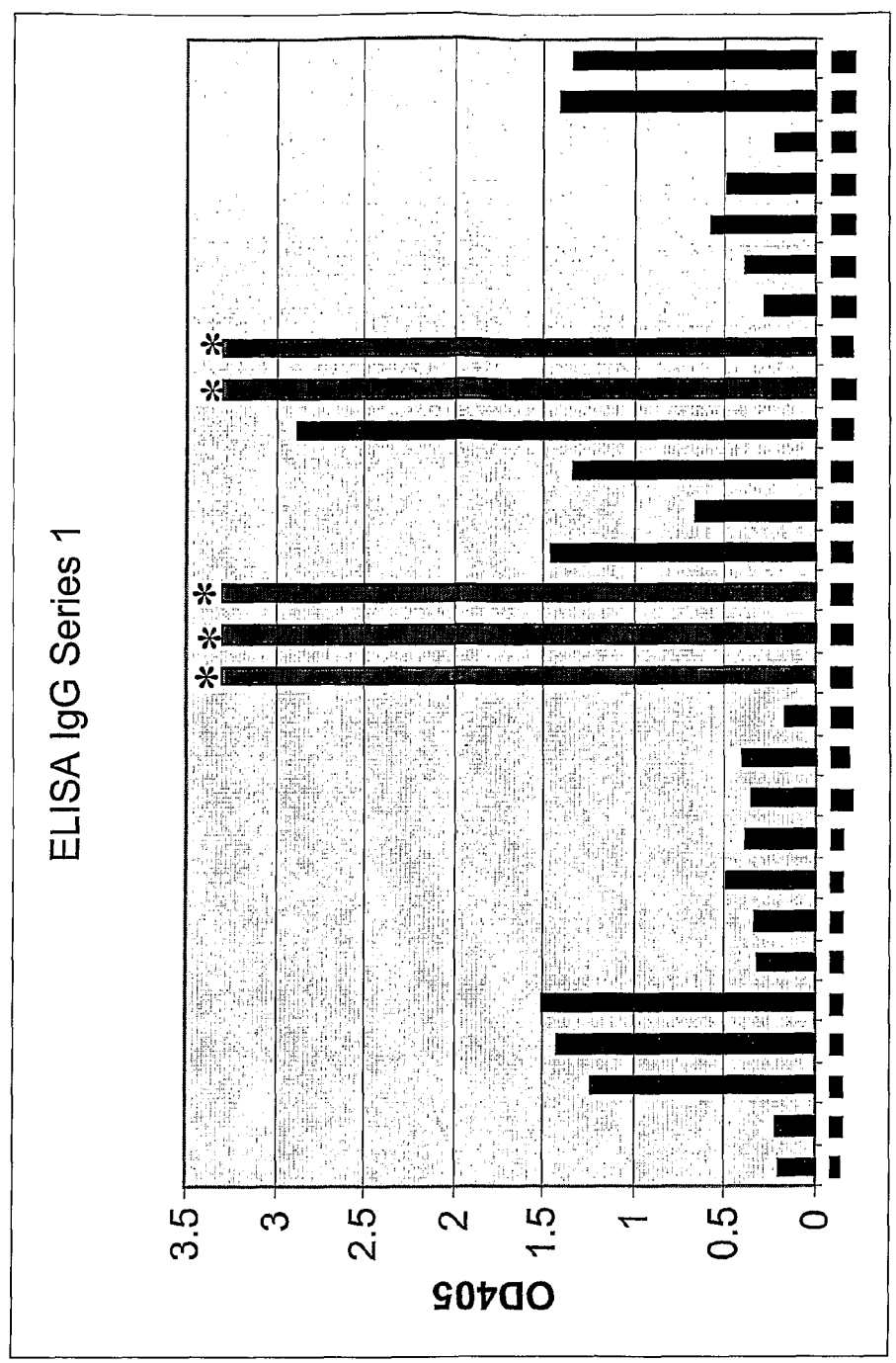
Figure 11A:
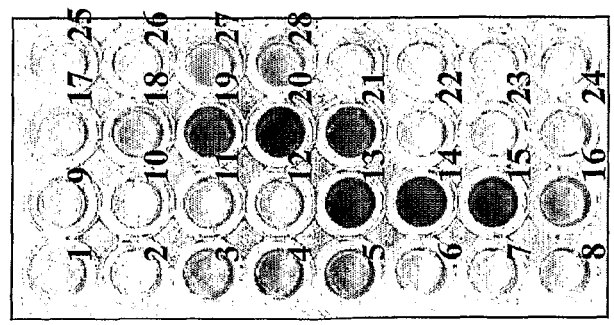

FIG. 11 (a) shows the results of an ELISA test for the determination of co-expression levels of IgG light and heavy chains using PVX and crTMV vectors. The numbering of the wells of the tissue culture plate on the left corresponds to the numbering of the bars in the histogram. The histogram displays the OD of the wells at 405 nm.

1, 2—uninfected plant tissue;
3, 4, 5—calreticulin SP-Heavy Chain in PVX (pICH21240-1, 5 and 14 clones, respectively);
6, 7, 8—calreticulin SP-Light Chain (LC) of IgG in PVX (deletion in N-terminus, pICH21370-18, 19, 31, respectively);
9, 10, 11—calreticulin SP-Light Chain of IgG in PVX (pICH21370-40, 44, 45, respectively);
12—blanc control (no plant protein extract applied);
13, 14, 15—calreticulin SP-Heavy Chain (HC) of IgG in PVX (pICH21240-1, 5 and 14 clones, respectively) co-expressed with calreticulin SP-Light Chain of IgG in crTMV (pICH 17620+pICH10881+pICH20431);
16, 17, 18—calreticulin-LC of IgG in PVX (deletion in N-terminus, pICH21370-18, 19, 31, respectively) co-expressed with calreticulin-HC in crTMV (PICH 17620+pICH10881+pICH20421);
19, 20, 21—calreticulin SP-LC of IgG in PVX (pICH21370-40, 44, 45, respectively) co-expressed with calreticulin SP-Heavy Chain in crTMV-based vector (pICH 17620+pICH10881+pICH20421);
22—GFP expressed with PVX (pIC0130);
23—GFP expressed with PVX (pICH20799);
24—calreticulin SP-Light Chain of IgG expressed from crTMV alone (pICH 17620+pICH10881+pICH20431);
25—calreticulin SP-Heavy Chain of IgG expressed from crTMV-based vector (pICH 17620+pICH10881+pICH20421);
26—Light and Heavy Chains of IgG co-expressed under control of strong 35S promoter at presence of PTGS suppressor P19;
27—IgG Light and Heavy Chains co-expression from crTMV-based vector (pICH17388+pICH10881=pICH20241);
28—Light and Heavy Chains co-expression from crTMV-based vector (pICH17388+pICH10881=pICH20241), MP (pICH10745) provided in trans;
*—OD405 value well above of measurable values.

Figure 11B:
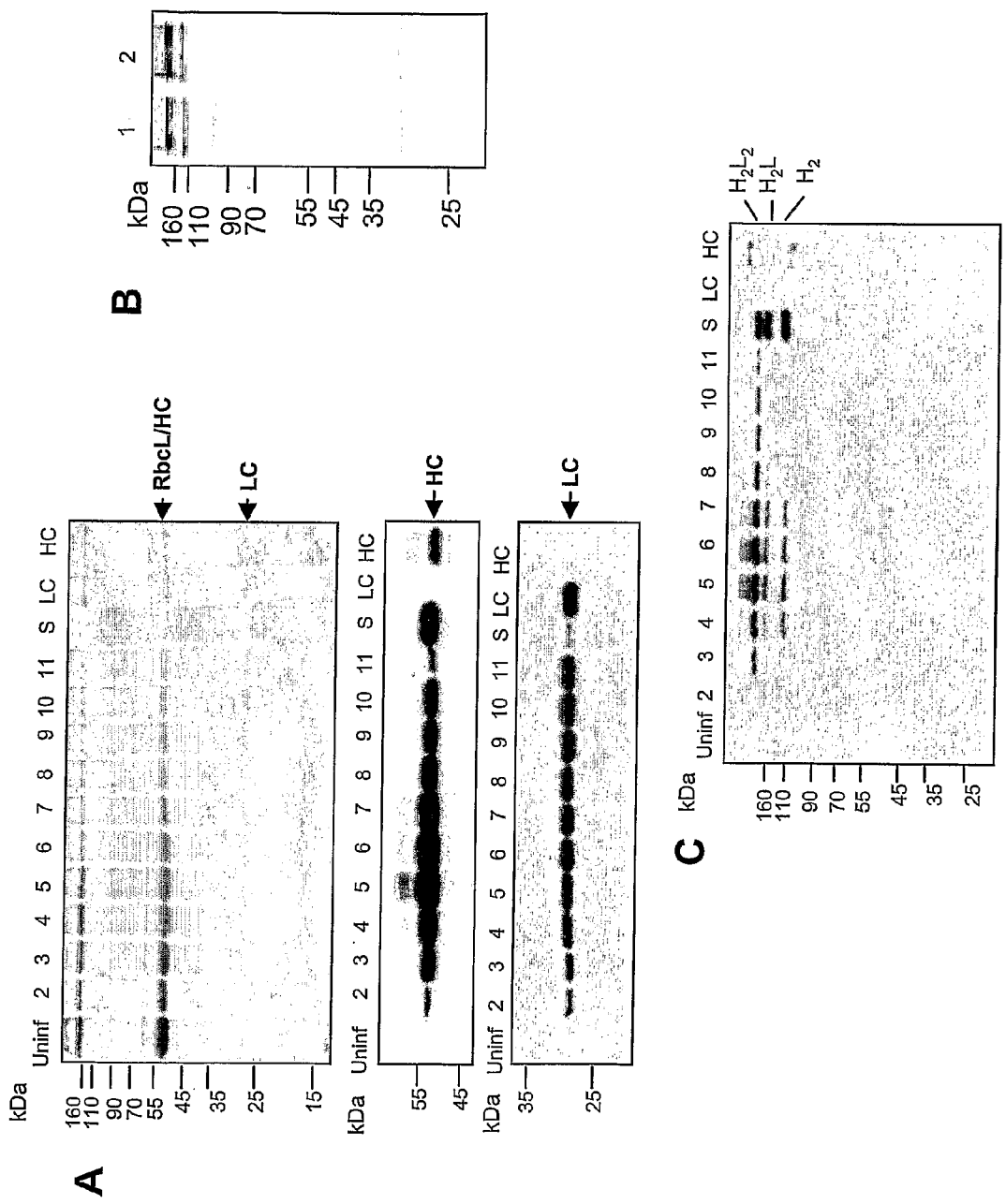

FIG. 11(b) shows electrophoretic and Western blot analysis of anti-cancer antibodies expressed in N. benthamiana leaves.

(A) Accumulation of heavy and light chains of an anti-cancer antibody in Nicotiana benthamiana leaves co-infected with TMV and PVX pro-vectors. Light chain is expressed with PVX and heavy chain with TMV. Proteins are separated in 12% polyacrylamide gel under reducing conditions. The upper panel shows coomassie staining; the middle panel shows a Western blot with HRP-conjugated goat anti-human IgG (gamma chain-specific) antibodies (Sigma); the lower panel shows a Western blot with HRP-conjugated rabbit anti-human IgG (lambda chain-specific) antibodies (Sigma). Uninf, uninfected tissue; 2-11, days post inoculation; S, anti-cancer mab (monoclonal antibody) standard; LC, light chain expressed alone with TMV pro-vectors (6 dpi); HC, heavy chain expressed alone with TMV pro-vectors (6 dpi).

(B) Purification of anti-cancer mab using Protein A Magnetic beads (NEB). (A) Plant-derived (lane 1) and standard (lane 2) mabs migrating in 12% polyacrylamide gel under the non-reducing conditions on Coomassie stained gel.

(C) Accumulation of assembled anti-cancer mab in Nicotiana benthamiana leaves co-infected with TMV pro-vector expressing the HC and PVX pro-vector expressing the LC. Proteins are separated in 10% polyacrylamide gel under the non-reducing conditions. The Western blot was probed with goat anti-human IgG (gamma chain-specific) antibodies. Uninf, uninfected tissue; 2-11, days post inoculation; S, anti-cancer mab standard; LC, light chain expressed alone with TMV pro-vectors (6 dpi); HC, heavy chain expressed alone with TMV pro-vectors (6 dpi). $H_2L_2$: IgG heterotetramer containing two heavy and two light chains, $H_2L$—heterotrimer containing two heavy and one light chains, $H_2$—heavy chain homodimer, $L_2$—light chain homodimer.

Figure 12:
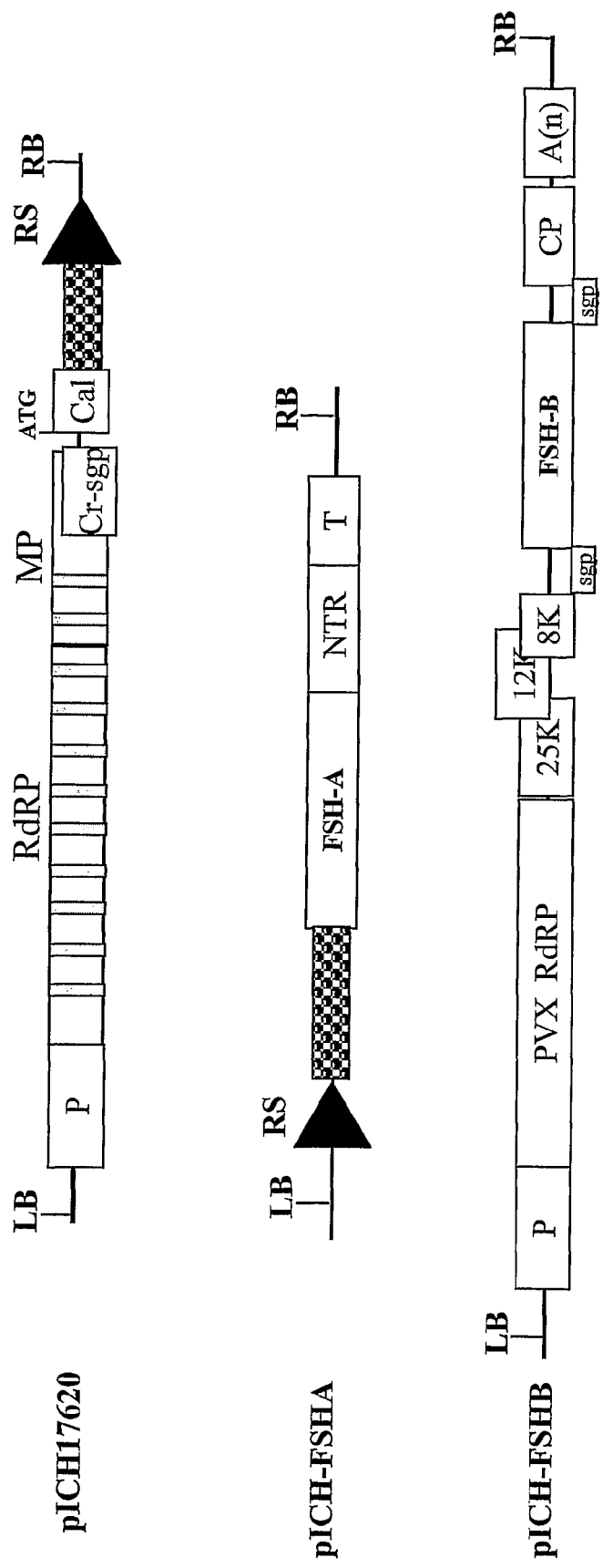

FIG. 12 shows a schematic representation of T-DNA regions of binary vectors pICH17620, pICH-FSHA and pICH-FSHB.

Figure 13:
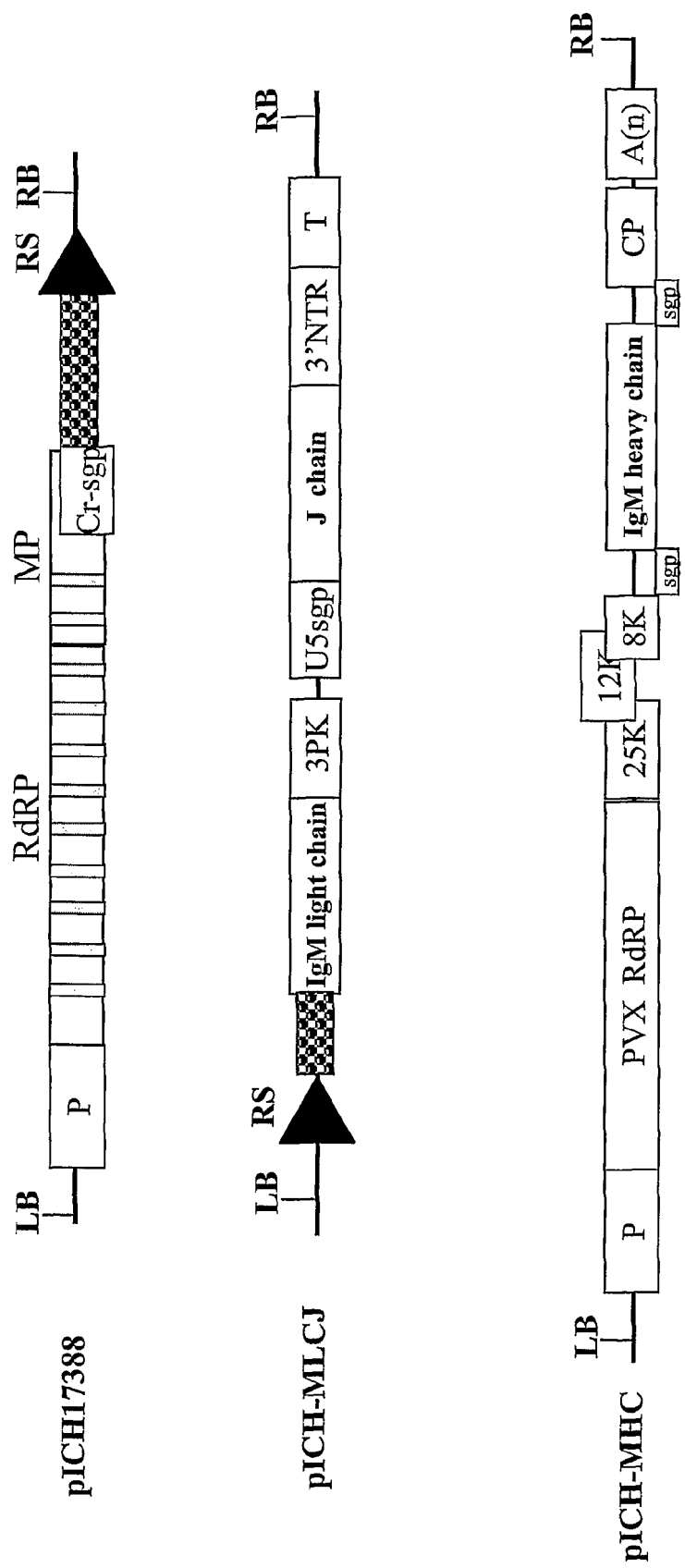

FIG. 13 depicts a schematic representation of T-DNA regions of binary vectors pICH17388, pICH-MLCJ and pICH-MHC.

DETAILED DESCRIPTION OF THE INVENTION

The viral vectors described in present invention are either viral vectors wherein a single vector encodes all protein subunits necessary for forming said hetero-oligomeric protein, or at least two different non-competing viral vectors, whereby each of said at least two viral vectors encodes for different protein subunit necessary for forming said hetero-oligomeric protein. Each of said non-competing viral vectors can express more than one heterologous nucleic acid sequence encoding more than one subunit of recombinant hetero-oligomeric protein. Said RNA viral vectors can be transiently delivered into plant cell or can be stably incorporated into plant chromosomal DNA as DNA precursor(s).

The present invention provides a process for high-yield production of hetero-oligomeric proteins in plant cells. This process overcomes the limitations of existing viral vector-based expression systems, such as size limitation for heterologous sequences to be expressed, high instability of said vectors and inability to co-express different heterologous nucleic acid sequences in the same plant cell. Further, said process offers better biosafety characteristics, as the removal of viral coat protein from the system prevents formation of infectious viral particles and reversion to wild type viruses. By practicing the invention, the design of high-yield expression system for hetero-oligomeric protein of interest is possible for practically any plant RNA virus-derived replicon, said replicon is suitable for the expression of a heterologous sequence of interest, through modification of said replicon to be capable expressing at least two heterologous sequences of interest encoding for different subunits of hetero-oligomeric protein of interest. Alternatively, another non-competing viral vector can be found that is able to co-replicate with said viral vector in the same plant cell.

Plus-sense single-stranded RNA viruses (also referred to herein as "RNA viruses" for brevity) belonging to different taxonomic groups are suitable for constructing the plus-sense single-stranded RNA viral vectors (also referred to herein as "viral vectors" for brevity) of this invention. Herein, a viral vector is an RNA vector capable of replicating in plant cells, i.e. forming further RNA vector molecules by RNA-dependent RNA polymerization using the RNA viral vector as a template. Preferably, the viral vectors of the invention contain at least one viral sequence element having an RNA viral function e.g. a replicase, a subgenomic promoter, an origin of viral particle assembly, a coat protein ORF, or a movement protein ORF. Further, the viral vector may have an RNA viral IRES element.

A viral vector can e.g. be constructed from the virus it is derived from by introducing restriction sites into the virus, said restriction sites representing cloning sites suitable for introducing the heterologous sequence of the invention. It will be understood by the skilled person that nucleic acid engineering on RNA viruses or vectors is generally done on the DNA level using DNA copies of said RNA viruses or vectors, respectively. Thus, it is more accurate to say that a DNA copy of an RNA viral vector can be constructed from the DNA copy of the RNA virus it is derived from by introducing restriction sites into the DNA copy of the RNA virus, said restriction sites representing cloning sites suitable for introducing the DNA copy of the heterologous sequence of the invention on the DNA level. These matters are obvious for a skilled person and will in general not be stressed herein.

If a DNA copy of an RNA virus naturally has (a) restriction site(s) suitable for cloning, the virus itself may be a viral vector. Herein, the term "viral vector" refers to the case where said heterologous sequence is not present in said vector or to the case where no sequence coding for a protein subunit of the invention is present in the vector. Cases wherein said heterologous sequence or a sequence coding for a protein subunit of the invention is inserted into said viral vectors are identified by explicitly specifying the presence of such insert.

Herein, two viral vectors are referred to as being different, if their sequences are different before said heterologous sequences or a sequence coding for a protein subunit of the invention have been introduced. Two viral vectors are referred to as being the same, if they have the same sequences before said heterologous sequences or a sequence coding for a protein subunit of the invention have been introduced. Thus, said heterologous sequences or sequences coding for the protein subunits of the invention are not taken into account when determining whether two viral vectors are different or the same.

Herein, the terms "replicon" or "viral replicon" have the same meaning as "viral vector".

A list of RNA viruses that can be used for engineering the viral vectors of the invention is presented below. Taxa names in quotes (and not in italic script) indicate that this taxon does not have an ICTV international approved name. Species (vernacular) names are given in regular script. Viruses with no formal assignment to genus or family are indicated):
RNA Viruses:
ssRNA Viruses:
Family: Bromoviridae,
Genus: Alfamovirus, Type species: alfalfa mosaic virus,
Genus: Ilarvirus, Type species: tobacco streak virus,
Genus: Bromovirus, Type species: brome mosaic virus,
Genus: Cucumovirus, Type species: cucumber mosaic virus;
Family: Closteroviridae,
Genus: Closterovirus, Type species: beet yellows virus,
Genus: Crinivirus, Type species: Lettuce infectious yellows virus,
Family: Comoviridae,
Genus: Comovirus, Type species: cowpea mosaic virus,
Genus: Fabavirus, Type species: broad bean wilt virus 1,
Genus: Nepovirus, Type species: tobacco ringspot virus;
Family: Potyviridae,
Genus: Potyvirus, Type species: potato virus Y, plum pox virus; tobacco etch virus; clover yellow vein virus; tobacco vein mottling virus;
Genus: Rymovirus, Type species: ryegrass mosaic virus,
Genus: Bymovirus, Type species: barley yellow mosaic virus;
Family: Sequiviridae,
Genus: Sequivirus, Type species: parsnip yellow fleck virus,
Genus: Waikavirus, Type species: rice tungro spherical virus;
Family: Tombusviridae,
Genus: Carmovirus, Type species: carnation mottle virus,
Genus: Dianthovirus, Type species: carnation ringspot virus,
Genus: Machlomovirus, Type species: maize chlorotic mottle virus,
Genus: Necrovirus, Type species: tobacco necrosis virus,
Genus: Tombusvirus, Type species: tomato bushy stunt virus,
Unassigned Genera of ssRNA Viruses,
Genus: Capillovirus, Type species: apple stem grooving virus;
Genus: Carlavirus, Type species: carnation latent virus;
Genus: Enamovirus, Type species: pea enation mosaic virus,
Genus: Furovirus, Type species: soil-borne wheat mosaic virus,
Genus: Hordeivirus, Type species: barley stripe mosaic virus,
Genus: Idaeovirus, Type species: raspberry bushy dwarf virus;
Genus: Luteovirus, Type species: barley yellow dwarf virus;
Genus: Marafivirus, Type species: maize rayado fino virus;
Genus: Potexvirus, Type species: potato virus X;
Genus: Sobemovirus, Type species: Southern bean mosaic virus,
Genus: Tenuivirus, Type species: rice stripe virus,
Genus: Tobamovirus, Type species: tobacco mosaic virus,
Genus: Tobravirus, Type species: tobacco rattle virus,
Genus: Trichovirus, Type species: apple chlorotic leaf spot virus;
Genus: Tymovirus, Type species: turnip yellow mosaic virus;
Genus: Umbravirus, Type species: carrot mottle virus;
Negative ssRNA Viruses: Order: Mononegavirales, Family: Rhabdoviridae, Genus: Cytorhabdovirus, Type Species: lettuce necrotic yellows virus,
Genus: Nucleorhabdovirus, Type species: potato yellow dwarf virus.

RNA viral vectors are able to provide an extremely high copy number of heterologous RNA providing for expression of the gene of interest in plant cell. However, it is known that such vectors become extremely unstable, if the size of heterologous nucleic acid sequence is increased beyond certain limits, usually beyond 1 kb. Due to such limitations the application of such vector systems has so far been restricted to the expression of relatively simple small to medium sized proteins. Attempts to express either large or complex hetero-oligomeric proteins have not led to a successful outcome. We have surprisingly found that viral vectors can be successfully adopted for the high-yield expression of complex hetero-oligomeric proteins, which has not been possible before. Early attempts to express full length monoclonal antibody (Verch et al., 1998, *J. Immunol. Meth.*, 220, 69-75) did not provide satisfactory results due to the incompatibility of the viral vectors used for co-expression of proteins of interest in the same cell. In Example 1 we demonstrate on single cell level that efficient co-expression of two different genes (GFP and DsRed) from viral replicons derived from the same plant RNA virus (TMV) is not possible. In FIG. 1 (A—right panel) we could not detect protoplasts that show expression of both reporter genes—DsRed and GFP. A weak expression pattern of DsRed in some protoplasts at right bottom panel coincides with strong GFP expression (right top panel) and is a false-positive result due to leakage of the filter used for DsRed detection. This leakage leads to an apparent weak DsRed fluorescence of protoplasts containing high concentrations of GFP. Thus, RNA replicons which are identical or share extensive regions of homology cannot co-exist in one plant cell even when they carry different heterologous nucleic acid sequences encoding for different recombinant proteins. The reason for this phenomenon is presently not known. A possible explanation is that the exponential increase in copy number of one viral replicons results in quick outcompetition of the other viral replicon. So a replicon which is second to start replication in a selected cell cannot catch up with the first one, whereby the events determining the "first" replicon are predominantly of statistical character.

In our studies to address this problem, we have engineered a viral replicon such that two different heterologous nucleic acid sequences encoding different proteins under control of two different subgenomic promoters are present in said replicon. The general scheme of a T-DNA region encoding such an RNA replicon is shown in FIG. 2. As a matter of convenience for design and optimisation of such a vector, we have used the pro-vector approach described in our earlier patent application (WO02088369; see also Marillonnet et al., 2004, *Proc. Natl. Acad. Sci. USA*, 101, 6852-6857). This approach allows to assemble in planta the final vector from pre-made modules via site-specific recombination, thus significantly speeding up vector design and vector optimisation. The design of the constructs is described in Example 2 and schematic representations are shown in FIG. 3.

We have surprisingly found that despite of the larger size of the insert in the final replicon and the complex structure of the vector due to the presence of two strong subgenomic promoters, the obtained RNA replicon showed high stability in planta and the ability to provide for co-expression of two different recombinant proteins (GFP and DsRed) in the same plant cell. As is shown in FIG. 4, the co-expression frequency can reach up to almost 100% of all cells in infected areas. Replacement of reporter genes (GFP and DsRed) e.g. with the light and heavy chains of an IgG in such a construct (FIG. 5) with further expression in infiltrated *N. benthamiana* leaves produced a surprising results. As is described in Example 3, a Western blot analysis revealed an impressively high concentration of assembled monoclonal antibodies (lanes 6 and 7; FIG. 6). The yield of assembled monoclonal antibody provided by our system is incomparably higher than that produced by current state of art system (FIG. 6, lane 4). To our knowledge, this is the first evidence of the expression of a complex hetero-oligomeric protein like an antibody using a plant viral vector-based expression system. All earlier publications were restricted to the expression of simple artificial derivatives of monoclonal antibodies, e.g. to the expression of single chain antibodies (scFv) using TMV-viral vectors (McCormick et al., 1999, *Proc Natl Acad Sci USA*, 96, 703-708; McCormick et al., 2003, *J. Immunol. Methods*, 278, 95-104) and PVX-based (Smolenska et al., 1998, *FEBS Lett.*, 441, 379-382; Franconi et al. 1999, *Immunotechnology*, 4, 189-201; Hendy et al., 1999, *J. Immunol. Methods*, 231, 137-146; Roggero et al. 2001, *Protein Expr. Purif.*, 22, 70-74).

In this invention, we preferably do not use systemic viral vectors. Instead of systemic viral vectors, we preferably replace the ability of the viral vector to move systemically by *agrobacterium*-mediated delivery of viral vector precursors into the plant system. This allows us to replace the viral coat protein with a heterologous sequence to be expressed. This approach contributes to the possibility of increasing the capacity of the viral vector for heterologous sequences. At the same time, this approach eliminates the probability of the viral vector to be converted to a wild type virus due to spontaneous deletion of heterologous sequences, which would compromise the productivity of the system.

Although our viral replicon-based system produced significantly better yield of monoclonal antibody than prior art systems, we examined the possibility of further increase the yield by decreasing the size of the viral replicon. Considering that there are limited possibilities to decrease the size of a viral replicon expressing two chains of a secretiory antibody, we have attempted the expression of heavy and light antibody chains from two different viral replicons. Considering that replicons based on the same virus are not able co-express two different heterologous sequences in the same plant cell (see above, example 1), we tested the possibility of co-expressing two different genes in the same plant cell by separately cloning DsRed and GFP genes into viral vectors derived from the non-homologous plant viruses tobacco mosaic virus (TMV) and Potato Virus X (PVX) (see Example 4). Schematic representation of T-DNA regions containing cDNAs of said viral vectors is shown in FIGS. 7 and 8 (PVX only). In Example 4, as a matter of convenience, we used a TMV-based viral vector assembled in planta from vector modules via site-specific recombination. Surprisingly, we have found that protoplasts isolated from a co-infiltrated plant leaf region showed practically 100% co-expression frequency of DsRed and GFP reporter genes (FIG. 9).

Recently, a study on the spatial separation of differently labelled viruses was presented by Dietrich and Maiss (2003, *J. Gen. Virology*, 84, 2871-2876). In this study, fluorescent proteins were expressed as reporters. Production of hetero-oligomeric proteins was not mentioned. Further, co-expression at the level of isolated protoplasts was not investigated. Since reporter gene products can diffuse to neighbouring cells via diffusion through plasmodesmata, no information was available whether the selected pairs of viruses expressed the reporter genes in the same or in neighbouring cells. The earlier publications relate to synergism between wild type viruses upon infection of plants, but do not relate to expression of hetero-oligomeric proteins in plant cells (Rochow & Ross, 1955, *Virology*, 1, 10-27; Goodman & Ross, 1974, *Virology*, 58, 16-24; Goodman & Ross, 1974, *Virology*, 59, 314-318; Goodman & Ross, 1974, *Virology*, 58, 263-271). Later development of these early studies on synergistic interactions of viruses in co-infected plants (Vance et al., 1995, *Virology*, 206, 583-590; Pruss et al., 1997, *Plant Cell*, 9, 859-868) led to the discovery of suppressors of post-transcriptional gene silencing (PTGS). The further development of recombinant protein expression systems was directed to study of such PTGS suppressors for enhanced production of recombinant proteins. There is no hint in the prior art to protein expression using viral expression systems based on synergistic viruses.

This invention demonstrates that non-competing viral vectors represent an efficient tool for the production of hetero-oligomeric proteins in plant cells or plants. Two or more viral vectors are non-competing with each other, if said viral vectors are capable of replicating in the same plant cell and do not dilute each other during said replication and transfection of other cells. Absence of dilution means that at least 10%, preferably 50%, more preferably 90%, and most preferably 100% of transfected plant cells are co-transfected, e.g. contain said two or more different viral vectors. Preferably, said viral vectors are capable of replicating and expressing heterologous nucleic acid sequences. More preferably, said heterologous nucleic acid sequences encode for different proteins. Even more preferably, said different proteins are subunits of hetero-oligomeric protein. In order to determine whether viral vectors are competing or non-competing, the frequency of co-transfection of plant cells can be measured. This can be done by the following protocol: two viral vectors are labelled with two different reporter genes, e.g. DsRed and GFP. Said differently labelled vectors are co-delivered (e.g. via agro-infiltration) into plant leaf tissue and 3-6 days later, the protoplasts isolated from the infected region can be counted in order to determine the proportion of protoplasts co-expressing both reporter genes compared to the number of protoplasts expression only one reporter gene. Experiments demonstrating such measurements are described in Examples 2 and 4 (see also the FIGS. 1A and 9). Usually, non-competing viral vectors can derive from viruses that are synergistic, e.g. can successfully co-transfect the same plant host. Examples of such pairs of synergistic RNA viruses include:
Potato Virus X (PVX)/Tobacco Mosaic Virus (TMV);
PVX/Tobacco Vein Mottling Virus (TVMV);
PVX/Tobacco Etch Virus (TEV);
PVX/Clover Yellow vein virus (CIYVV);
PVX/Plum Pox Virus (PPV);
PVX/Potato Virus Y (PVY).

The mechanistic reason for competitiveness or non-competitivness of viral vectors is not known. One possible explanations is that viral replicons derived from synergistic viral vectors form viral replication complexes (VRCs) (Kawakami et al, 2004, *Proc. Natl. Acad. Sci. USA*, 101, 6291-6296) at different sub-cellular compartments, thus they are not competing with each other for the space necessary for forming VRCs. As it was established experimentally, non-competing viral vectors may be derived from different species of viruses that are significantly different at the level of their nucleic acid sequences. Said non-competing viral vectors can be derived from synergistic plant viruses that can successfully co-infect the same plant host. Synergistic viruses usually belong to different genuses. For example, PVX belongs to the genus Potexvirus, while viruses synergistic thereto like TVMV, TEV, PPV, and CIEVV belong to the genus Potyvirus. Other viruses synergistic (non-competing) to PVX viruses, like TMV, TVCV, and crTMV belong to the genus Tobamovirus. Obviously, the genome homology between representatives of different genuses is rather low, usually below 50% identity on the RNA level.

Cloning of heavy and light chains of a monoclonal antibody into different viral vectors (e.g. PVX and TMV-based) following further co-expression of said chains in co-infected plant tissue is described in Example 5. Schematic representations of the vectors is shown in FIG. 10. Comparative ELISA measurement of yield of monoclonal antibodies produced with help of this and other expression systems showed the best performance of said system based on two non-competing viral vectors (FIG. 11). Efficient expression of recombinant hetero-oligomeric proteins in plant cell with the help of viral vector(s) is not known in the prior art.

Based on our data, virus-derived sequences of the viral vectors shall not exhibit homology significant enough to consider said viruses related to each other. An example of such viruses is the virus pair TMV and PVX and viral vectors based thereon. These viral vectors exhibit no such homology. Another requirement for selecting acceptable virus pairs can be the synergism of the original wild type viruses during co-infection of a plant host.

The experiments discussed above were done with transient expression systems based on *Agrobacterium*-mediated DNA precursor delivery into plant cells. However, an alternative application of this invention is for transgenic plants with a DNA precursor of said RNA replicon(s) stably incorporated into a plant nuclear chromosome. This allows to overcome many limitations of plant viral vector-based systems, such as the restrictions to the maximal size of heterologous sequences viral vectors can tolerate. As the DNA precursor will be present in each cell of the transgenic plant, there is no absolute requirement for systemic movement or for cell to cell movement of the RNA replicon (replicon spreading). This can be compensated by the high efficiency of formation and transport of the RNA replicons of the invention into the cytoplasm. However, the ability of the vector for cell-to-cell movement can be of an additional value, as RNA replicon formation does not always occur in all cells.

Different methods may be used for providing a plant, plant tissue or plant cells with heterologous DNA. Said vectors may be transformed into plant cells by a Ti-plasmid vector carried by *Agrobacterium* (U.S. Pat. No. 5,591,616; U.S. Pat. No. 4,940,838; U.S. Pat. No. 5,464,763) or particle or microprojectile bombardment (U.S. Pat. No. 5,100,792; EP 00444882B1; EP 00434616B1). Other plant transformation methods can also be used like microinjection (WO 09209696; WO 09400583A1; EP 175966B1), electroporation (EP00564595B1; EP00290395B1; WO 08706614A1) or PEG-mediated transformation of protoplasts etc. The choice of the method for vector delivery may depend on the plant species to be transformed. For example, microprojectile bombardment is generally preferred for monocot transformation, while for dicots, *Agrobacterium*-mediated transformation gives better results in general.

In the examples of the invention, we used transient *Agrobacterium*-mediated delivery of vectors (said heterologous DNA) into *Nicotiana* cells. However, said vectors may be stably introduced into the plants in accordance with any of the standard techniques suitable for stable or transient transformation of the plant species of interest. Transformation techniques for dicotyledonous are well known in the art and include *Agrobacterium*-based techniques and techniques which do not require *Agrobacterium*. Non-*Agrobacterium* techniques involve the uptake of exogenous genetic material directly by protoplasts or cells. These techniques include PEG or electroporation mediated uptake, particle bombardment-mediated delivery and microinjection. Examples of these techniques are described in Paszkowski et al. *EMBO J* 3, 2717-2722 (1984), Potrykus et al., *Mol. Gen. Genet.* 199, 169-177 (1985), Reich et al., *Biotechnology* 4:1001-1004 (1986), and Klein et al., *Nature* 327, 70-73 (1987). In each case, the transformed cells are regenerated to whole plants using standard techniques.

*Agrobacterium*-mediated transformation is a preferred technique for the transformation of dicotyledons because of its high transformation efficiency and its broad utility with many different species. The many crop species which may be routinely transformed by *Agrobacterium* include tobacco, tomato, sunflower, cotton, oilseed rape, potato, soybean, alfalfa and poplar (EP 0 317 511 (cotton), EP 0 249 432 (tomato), WO 87/07299 (Brassica), U.S. Pat. No. 4,795,855 (poplar)).

In the examples of this invention, *Agrobacterium*-mediated delivery of T-DNA for transient expression of gene(s) of interest (Vaquero et al., 1999, *Proc. Natl. Acad. Sci. USA*, 96, 11128-11133) was employed. This method is an extremely useful tool not only for small-to-middle scale recombinant protein production systems, but also for large-scale expression.

Release of viral replicon precursor stably incorporated into plant chromosomal DNA can be achieved using inducible or any other regulated (e.g. developmentally regulated) promoter. Inducible promoters can be divided into two categories according to their induction conditions: those induced by abiotic factors (temperature, light, chemical substances) and those that can be induced by biotic factors, for example, pathogen or pest attack. Examples of the first category are heat-inducible (U.S. Pat. No. 5,187,287) and cold-inducible (U.S. Pat. No. 5,847,102) promoters, a copper-inducible system (Mett et al., 1993, *Proc. Natl. Acad. Sci.*, 90, 4567-4571), steroid-inducible systems (Aoyama & Chua, 1997, *Plant J.*, 11, 605-612; McNellis et al. 1998, *Plant J.*, 14, 247-257; U.S. Pat. No. 6,063,985), an ethanol-inducible system (Caddick et al., 1997, *Nature Biotech.*, 16, 177-180; WO09321334), and a tetracycline-inducible system (Weinmann et al., 1994, *Plant J.*, 5, 559-569). One of the latest developments in the area of chemically inducible systems for plants is a chimaeric promoter that can be switched on by glucocorticoid dexamethasone and switched off by tetracycline (Bohner et al., 1999, *Plant J.*, 19, 87-95). For a review on chemically inducible systems see: Zuo & Chua, (2000, *Current Opin. Biotechnol*, 11, 146-151) and Padidam, M (2003, *Curr. Opin. Plant Biol*, 6, 169-177). Other examples of inducible promoters are promoters, which control the expression of patogenesis-related (PR) genes in plants. These promoters can be induced by treatment of a plant with salicylic acid, an important component of plant signaling pathways in response to pathogen attack, or other chemical compounds (benzo-1,2,3-thiadiazole or isonicotinic acid) which are capable of triggering PR gene expression (U.S. Pat. No. 5,942,662).

This invention is not limited to TMV and PVX-based vectors described in the examples, but is applicable to replicons derived from other plant RNA viruses, subject to the establishment of expression systems derived from said viral replicons. The best studied synergism in co-infected plants is known for the PVX/PVY pair of viruses (Rochow & Ross, 1955, *Virology*, 1, 10-27; Goodman & Ross, 1974, *Virology*, 58, 16-24). It is very likely that many of those viruses can co-replicate in the same plant cell. Dietrich & Maiss (2003, *J. Gen. Virol.*, 84, 2871-2876) have shown that differently labelled pairs of viruses, e.g. plum pox virus (PPV) and potato virus X (PVX), tobacco vein mottling virus (TVMV) and PVX, Clover yellow vein virus (CIYVV) and PVX, can co-express different reporter genes in the same infected region of plant tissue. Using the strategy described in this invention, recombinant hetero-oligomeric protein expression systems for practically any pair of plant plus-sense single-stranded RNA virus-derived replicons that are capable of co-replication in the same plant cell can be developed. For example, viral vectors based on alfalfa mosaic virus (AMV) of the genus alfamovirus can be used in this invention.

Genes of interest encoding for complex (hetero-oligomeric) proteins, their fragments (functional or non-functional) and their artificial derivatives and fusions can be expressed in plants or plants cells using the present invention. Many commercially valuable groups of hetero-oligomeric proteins can be produced and purified using the invention. Those groups include but not limited to industrial and research proteins as well as proteins for applications in the area of human or animal health. However, the most preferred is the group of immune response proteins, specifically—monoclonal antibodies selected from different classes of immunoglobulins (IgG, IgM, IgA and IgD) and their synthetic derivatives like mutant versions and different types of fusions with other proteins or parts thereof.

EXAMPLES

The following examples are presented to illustrate the present invention. Modifications and variations may be made without departing from the spirit and scope of the invention.

Example 1

Figure 1C:
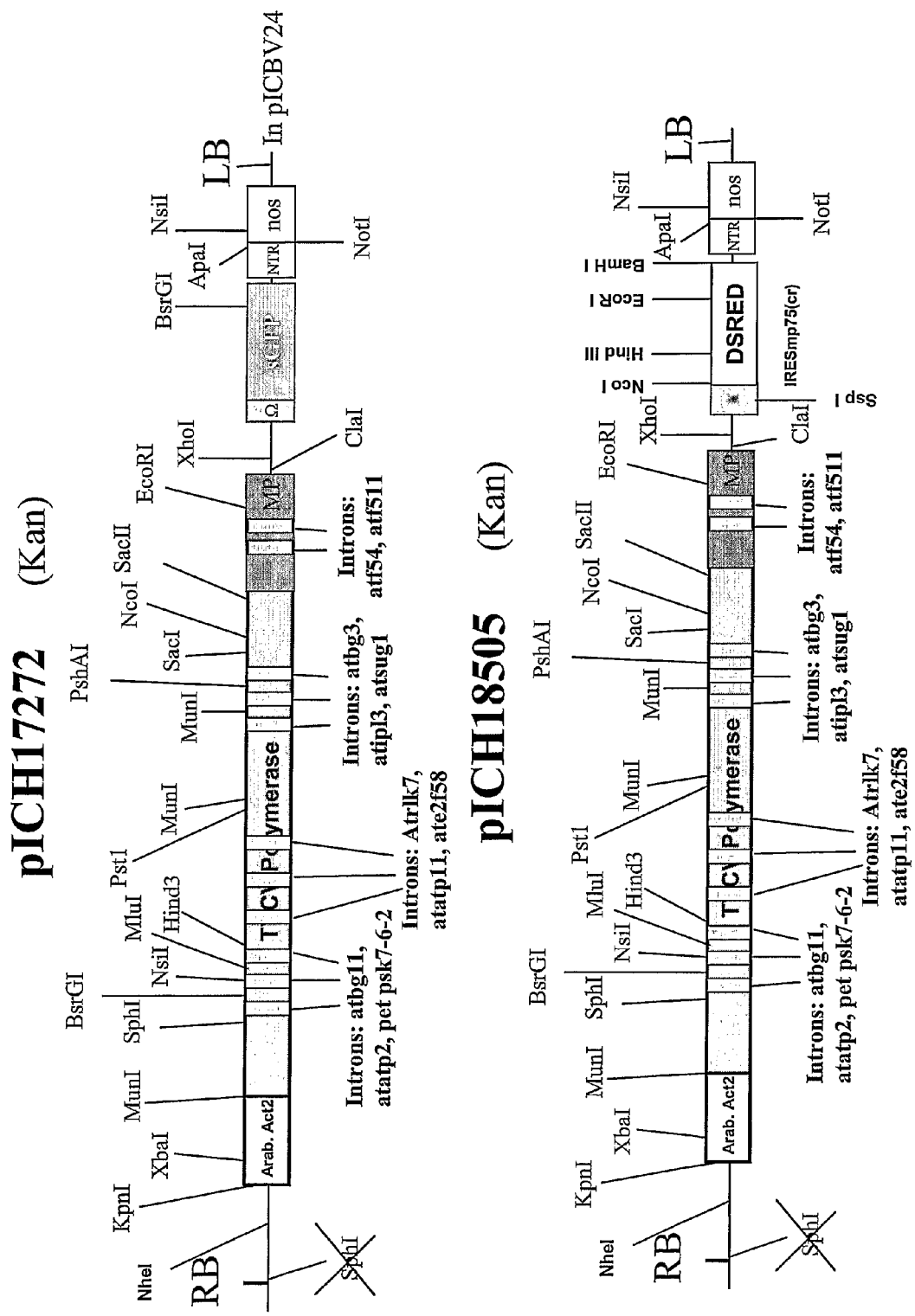
FIG. 1 (A) shows an expression distribution pattern of GFP and DsRed from two different TMV-based vectors in infiltrated *N. benthamiana* leaves. Left picture: the light spot at the top left side is GFP fluorescence of an area infiltrated with pICH17272. The weakly light spot below is red fluorescence of an area infiltrated with vector pICH18505. The light spot at the bottom right side of the left picture is an area infiltrated with pICH17272+pICH18505. The pictures on the right hand side show protoplasts isolated from a leaf area co-infiltrated with two different vectors (top: protoplasts under GFP fluorescence detection conditions; bottom panel: the same protoplasts under DsRed fluorescence detection conditions.

Lack of Co-Expression of GFP and DsRed from Two TMV-Based RNA Viral Vectors that are Derived from the Same Plant RNA Virus Leaf tissue was infected with two TMV-based viral vectors derived from the same plant RNA virus but containing two different genes of interest (FIG. 1). We tested this approach using the visual marker genes GFP and DsRed cloned into a TMV-based viral vector. The first construct, pICH17272 (see FIG. 1 of Marillonnet et al., 2005, *Nat. Biotechnol.*, 23, 718-723), contains GFP, and is similar to pICH18711 (see International patent application PCT/EP03/12530, published as WO2005049839; Marillonnet et al., 2005, *Nat Biotechnol.*, 23, 718-723) with the exception that the RdRP coding sequence in the vector contains 9 plants introns rather than 14. The pICH18722 (Marillonnet et al., 2005, *Nat. Biotechnol*, 23, 718-723) is built on the backbone of two closely related strains of TMV, Cr-TMV (Dorokhov et al. 1994, *FEBS Lett* 350, 5-8) and TVCV (Lartey et al., 1994, *Arch. Virol.* 138, 287-298), and contains the viral genome placed under control of a plant promoter, with the coat protein sequence replaced by a heterologous sequence. The presence of 11 introns in the RdRP and MP increases the efficiency of initiation of viral replication after *agrobacterium*-mediated delivery of the vector to leaf tissue, and therefore increase the probability of co-expression of the two viral vectors in the same cell. The pICH18505 is similar to pICH17272 except that the GFP coding sequence has been replaced by the coding sequence of DsRed using Xho 1-Not 1 restriction sites (FIG. 1). Detailed restriction maps of T-DNA regions of pICH18505 and pICH17272 are shown in FIG. 1C. pICH17272 and pICH18505 were transformed in *Agrobacterium* strain GV3101, and leaf tissue was infiltrated into *Nicotiana benthamiana* as previously described (Marillonnet et al., 2004, *Proc. Natl. Acad. Sci. USA*, 101, 6852-6857). Protoplasts were prepared from the infiltrated area 7 days post infiltration (dpi) and observed under blue or red light under the microscope. Very few protoplasts expressed both GFP and DsRed (FIG. 1A), even when protoplasts were prepared from the infiltrated area several days later. This suggests that once a cell becomes infected with a first TMV-based viral vector, it becomes unable to be reinfected by a second TMV-based vector.

Example 2

Co-Expression of GFP and DsRed from a Single Viral Replicon

Two genes of interest were expressed from an RNA viral vector, under control of two separate subgenomic promoters (FIG. 2). Both subgenomic promoters can be identical, but to avoid the risk of deletion between repeated sequences in the construct during viral replication, it is preferred to use subgenomic promoters from related TMV strains; in this case, the second subgenomic promoter and 3' non-translated region comes from TMGMV strain U5 (Shivprasad et al, 1999, *Virology*, 255, 312-323; Marillonnet et al., 2004, *Proc. Natl. Acad. Sci. USA*, 101, 6852-6857). Also, for convenience of cloning, GFP and DsRed were cloned in viral provectors (described in WO02/088369 and by Marillonnet et al. 2004, *Proc. Natl. Acad. Sci. USA*, 101, 6852-6857), rather than in a complete assembled vector. The two provectors, pICH17388 and pICH15933 (FIG. 3), were converted to a fully functional TMV-based viral vector by site-specific recombination between both provector modules in planta. pICH17388 is similar to pICHNOP (Marillonnet et al., 2004, *Proc. Natl. Acad. Sci. USA*, 101, 6852-6857) with the exception that 11 introns are present in viral sequences (as in pICH17272). pICH15933 is equivalent to pICHGFPSYS (Marillonnet et al. 2004, *Proc. Natl. Acad. Sci. USA*, 101, 6852-6857) except that the coding sequence of TMGMV U5 was replaced by the coding sequence of DsRed.

The pICH15933 was transformed in *Agrobacterium* strain GV3101 and infiltrated in *Nicotiana benthamiana* leaf together with pICH17388 and pICH10881 (FIG. 3). Five days after infiltration, all GFP-expressing foci were also expressing DsRed showing excellent coexpression of two genes in the same plant cells (FIG. 4).

Example 3

Expression of an Antibody from a Single Viral Replicon

The coding sequences of GFP and DsRed in pICH15933 were replaced by the IgG antibody light and heavy chains, respectively, resulting in construct pICH20241 (FIG. 5). As a control, the heavy and light chains were cloned in a TMV-based provector, replacing the coding sequence of pICH1740, resulting in constructs pICH20421 and pICH20431 (FIG. 5). The pICH20241 was coinfiltrated in *Nicotiana benthamiana* leaves together with pICH17388 and pICH10881 (FIG. 3).

Western blot analysis of total soluble protein extracted from infiltrated leaves was performed with 1:6000 diluted anti-human IgG rabbit antibodies labelled with horseradish peroxidase (HRP) (Sigma). The results of the analysis are shown in FIG. 6A. It is evident that the expression level of an antibody achieved with the help of a single viral vector (lanes 6 & 7, FIG. 6) is significantly higher than that achieved with the help of a strong constitutive promoter even in the presence of the PTGS suppressor P19 (lanes 3-4, FIG. 6).

Example 4

Co-Expression of GFP and DsRed with TMV- and PVX-Based Viral Vectors

An other strategy for coexpression of two genes is to use separate viral vectors built on different viruses that can coinfect and replicate in the same cell. As an example, an expression vector based on potato virus X (PVX) can coexist in the same cell with TMV. Schematic representations of two such non-competing viral vectors are shown in FIG. 7.

Inoculum of PVX (strain PV0014) was obtained from the German Collection of Microorganisms and Cell Cultures (DSMZ) as infected dry leaf material, and was used for inoculation of *Nicotiana bentamiana* plants. Systemic leaves of inoculated plants that exhibited viral symptoms were used for preparation of total RNA. $1^{st}$ strand cDNA was made using primers pvxpr2, pvxpr4 and pvxpr6. Three cDNA fragments were amplified by PCR from PVX cDNA using a Pfu-Taq polymerase mix:

Fragment 1 Amplified with Primers:

```
pvxpr1:  ttt ggtctc a tgaa gaaaactaaaccatacaccaccaacacaac   (SEQ ID NO:
                                                            1)

Pvxpr2:  ctttttccagcccggagaccatttctgtgatgg                  (SEQ ID NO:
                                                            2)
```

Fragment 1 Digested with BsaI.
Fragment 2 Amplified with Primers:

```
Pvxpr3:  ttt cgtctc a gggctggaaaaagaggacttccctgaagg         (SEQ ID NO:
                                                            3)

Pvxpr4:  gagtcgtctcctgcataaacttgagcag                       (SEQ ID NO:
                                                            4)
```

Fragment 2 Digested with Esp3I
Fragment 3 Amplified with Primers:

```
Pvx5:  ttt gaagac aa tgcaggagacgactccgcactgg                (SEQ ID NO:
                                                            5)

Pvx6:  cg gacgtc ttttttttttttttttttttttt atttatattattcatacaatcaaaccagaaaatac   (SEQ ID NO:
                                                                                6)
```

Fragment 3 Digested with BpiI AatI

Fragment 4 containing Arabidopsis actin2 gene promoter, (An et al. 1996, *Plant J.*, 10, 107-121) was amplified from Arabidopsis genomic DNA with primers:

```
Act2pr1: ttt acgcgt ttcgacaaaatttagaacgaacttaattatg    (SEQ ID NO:
                                                       7)

Act2pr2: ttt ggtctc a ttca ttcaaagcggagaggaaaatatatg   (SEQ ID NO:
                                                       8)
```

Fragment 4 Digested with Mlul and BsaI.

Figure 10A:
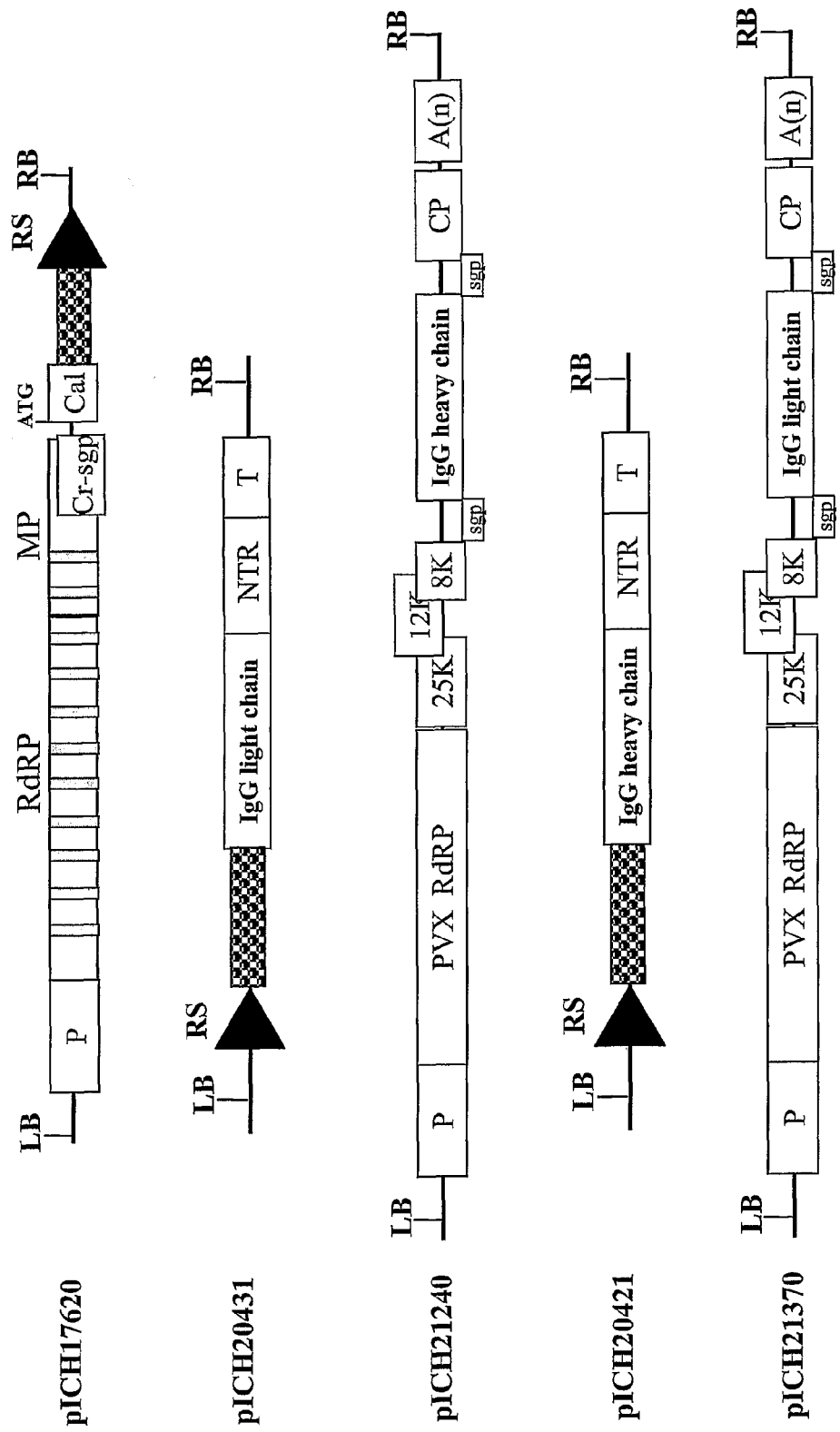
Figure 10B:
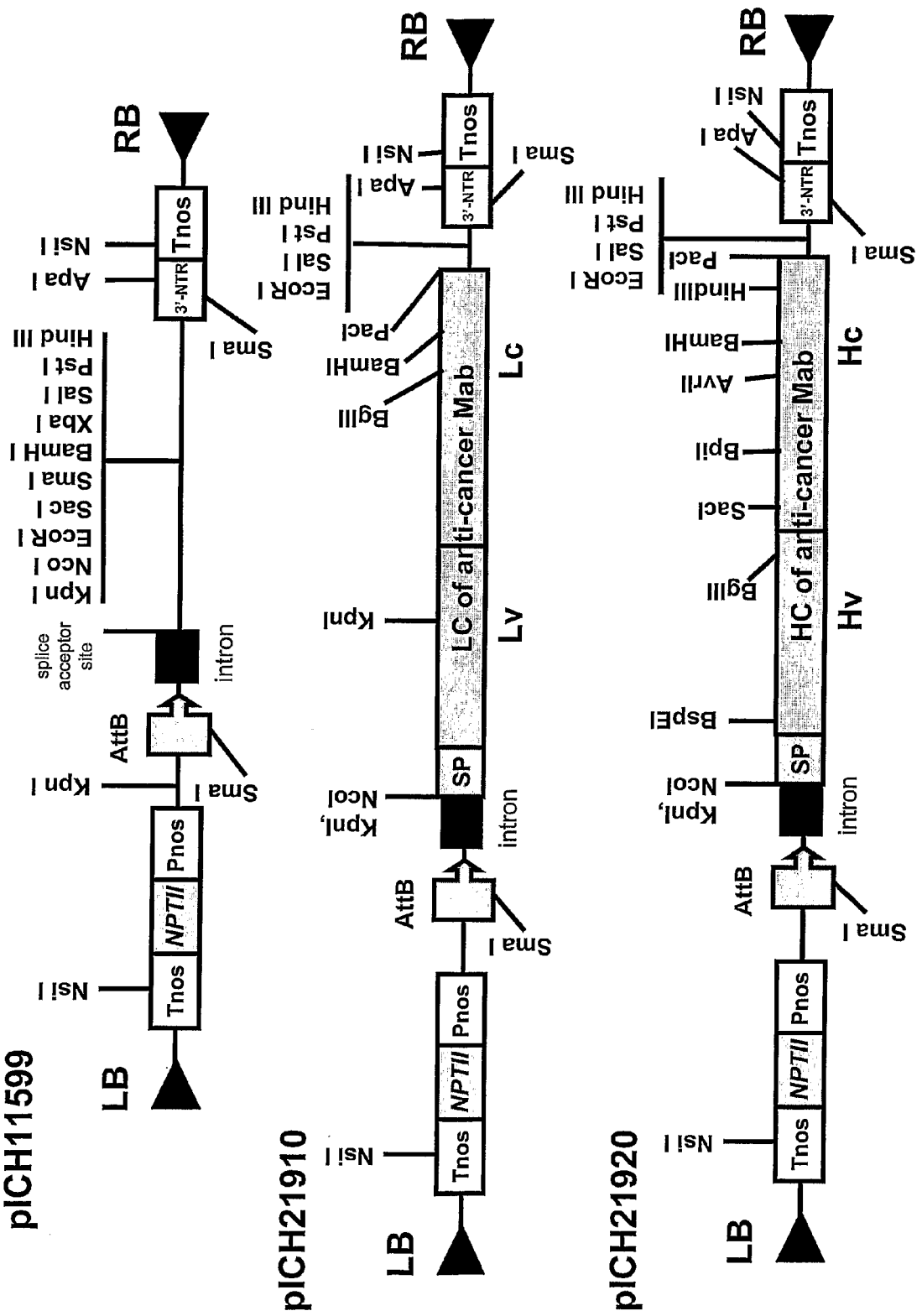
Figure 10C:
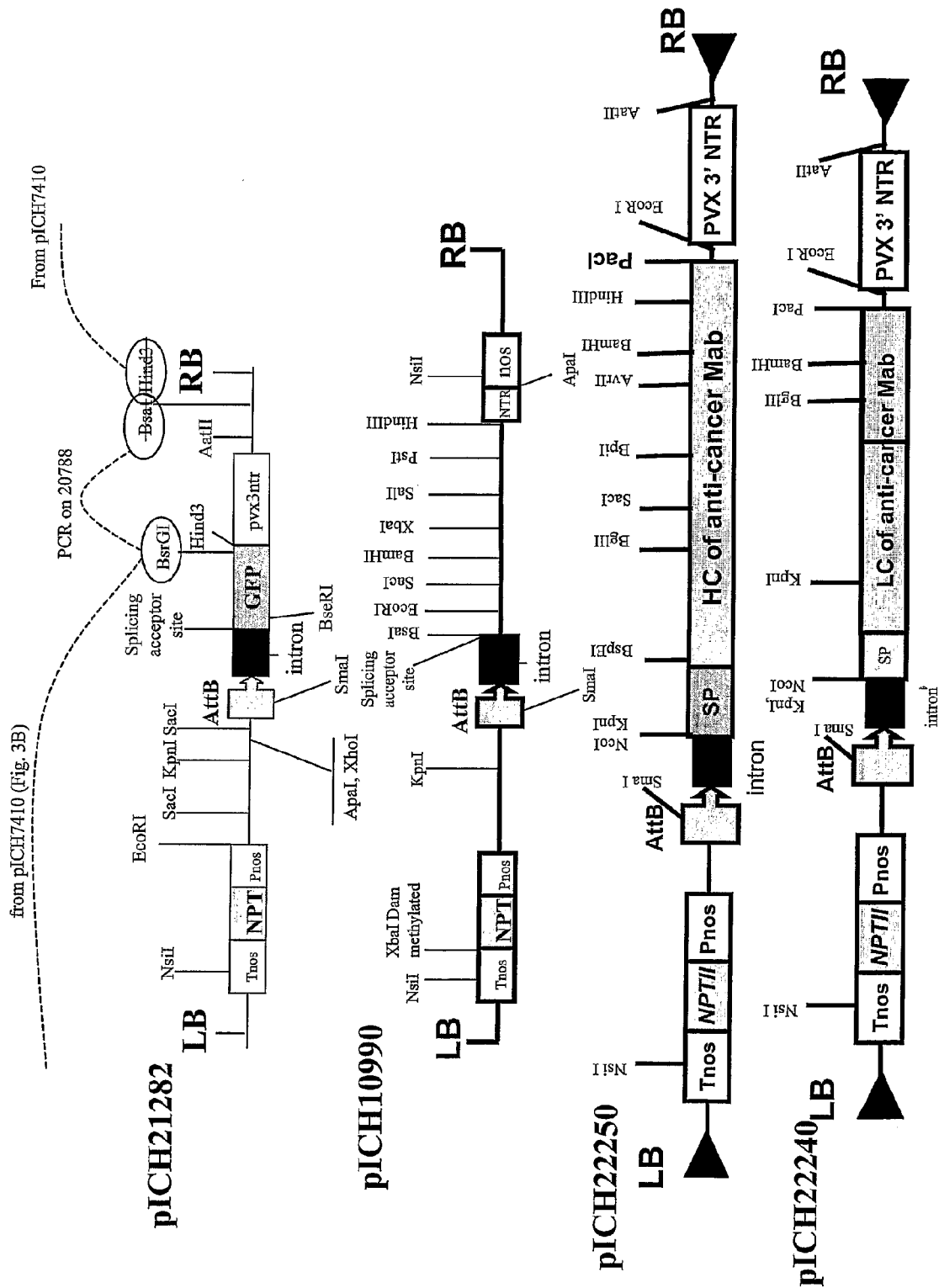
Figure 10D:
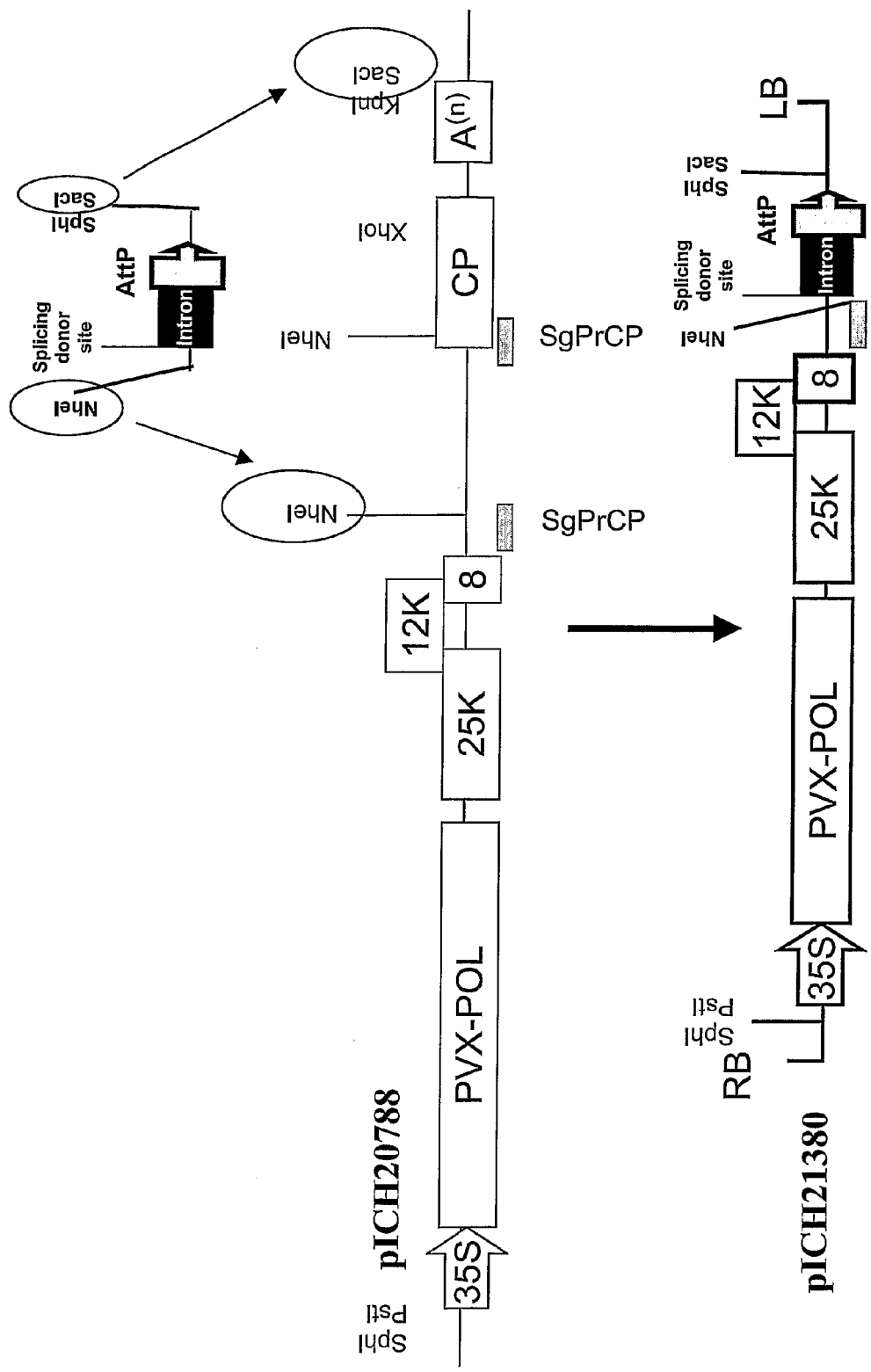

As an alternative to the Arabidopsis Actin 2 promoter, the CaMV 35 promoter was also used to drive transcription of PVX-based viral vector (see FIG. 10D, pICH20788; pICH21380). The general strategy of making PVX-based vectors was used as described by Baulcombe and colleagues, (1995, *Plant Journal*, 7:1045-1053).

All four fragments were cloned together in a binary vector digested with Mlu1 and AatII. 20 clones of the resulting construct were transformed in *Agrobacterium* strain GV3101 and each clone infiltrated into one leaf of a *Nicotiana benthamiana* plant. One week later, *Nicotiana benthamiana* were phenotypically screened for viral infection symptoms, and the positive plasmid clones saved (pICHPVX).

A cloning vector was made from this complete functional cDNA for cloning a gene of interest downstream of the CP subgenomic promoter. The GFP gene was cloned as an example. An ATG in the CP subgenomic promoter area was mutated to AGG (position 5651 in Genbank accession M95516). The GFP gene was cloned 3' of the NheI site (coordinates 5662 to 5667). The 3' end of PVX (coordinates 5618 to 6435) was cloned downstream of the GFP sequence, and this sequence was followed by a stretch of 12 to 24 A). This construct (pICH0130, FIG. 8) was agroinfiltrated into *Nicotiana benthamiana* leaf. GFP fluorescence appeared in the infiltrated area two to three days after infiltration. Systemic movement of GFP appeared a few days later.

The pIC0130 was coinfiltrated into *Nicotiana benthamiana* leaf together with vectors pICH17388, pICH10580 and pICH10881 (FIG. 3) providing for expression of DsRed. Six days after co-infiltration, protoplasts were prepared from the infiltrated area and observed under the microscope under blue light. Nearly all protoplasts expressed both GFP and dsRed, showing excellent level of coexpression FIG. 9).

Example 5

Expression of a Monoclonal Antibody with TMV and PVX-Based Vectors

The heavy and light chains of the IgG were cloned in a PVX vector, replacing the coding sequence of GFP in pIC0130, generating two constructs, pICH21240 and pICH21370, containing either the heavy or the light chain, respectively (FIG. 10 A). Clones of TMV provector parts containing either the light or the heavy chain of antibody were also constructed (pICH20431 and pICH20421, FIG. 10A). Mixture of agrobacteria providing for two different chains expressed form PVX and TMV-based vectors were infiltrated into *N. benthamiana* leaves and the expression level of antibodies were measured by ELISA 10 days after inoculation. Results (FIG. 11) show an extremely high level of assembled functional antibodies in case of co-expression of heavy and light chains from PVX and TMV-based vectors. These levels were significantly higher than those obtained from a TMV vector expressing both chains (EXAMPLE 3).

Yet another human tumor-specific monoclonal antibody belonging to IgG1 subclass, anti-cancer mab, was subcloned into TMV and PVX-based vectors as follows: The 730 NcoI-NotI fragment, containing the anti-cancer mab light chain coding sequence was blunted at NotI site and ligated into TMV-based 3' module cloning vector pICH11599 (FIG. 10B) opened with NcoI-XbaI and blunted at the XbaI site resulting in pICH21910 (FIG. 10B). The same strategy was used to subclone the 1421 bp NcoI-NotI fragment with the anti-cancer mab heavy chain coding sequence into pICH11599 (FIG. 10B) that resulted in the pICH21920 (FIG. 10B) construct. PVX-based 3' module for GFP expression pICH21282 (FIG. 10C) was created on the basis of TMV-based 3' module cloning vector pICH10990 (FIG. 10C). It was achieved in several cloning steps via insertion of GFP coding sequence into pICH10990 (FIG. 10C) and consequent replacement of TMV 3' untranslated region with 3' untranslated region of PVX. Similarly, TMV-based 3' pro-vector module pICH21920 (FIG. 10B) was converted into PVX-based 3' pro-vector construct pICH22250 (FIG. 10C) by replacement of TMV 3' untranslated region with 3' untranslated region of PVX. It was achieved by ligation of the 575 bp HindII-NdeI fragment of pICH21282 (FIG. 10C) blunted at the HindIII site with SalI-NdeI fragment of pICH21920 blunted at the SalI site. A 723 bp NcoI-EcoRI fragment containing coding sequence of anti-cancer mab light chain was subcloned into pICH22250 (FIG. 10C) digested with NcoI-EcoRI, resulting in pICH22240 (FIG. 10C).

The 5' provector pICH21380 (FIG. 10D) was made in the following way: construct pICH17388 (FIG. 3B) was used as template to PCR amplify the fragment with the help of primers pv5p5F (SEQ ID NO: 9) (5' cagctagcaa caaacaagaa aggtaagttt c-3') and pv5p5R (SEQ ID NO: 10) (5'-tctgagctct gcatgctacg cccccaactg agag-3'), digested with Nhe1 and Sac1 restriction enzymes and ligated with large Nhe1-Sac1 fragment of pICH20788, replacing 3' part of PVX vector with 5' end of intron and AttP recombination site. The scheme of cloning is shown in FIG. 10D. The strategy of using 5' provectors with 3' provectors in order to assemble a viral vector in planta via site-specific recombination was as described earlier (Marillonnet et al, 2004, *Proc. Natl. Acad. Sci. USA*, 101:6852-6857).

Agroinfiltration Procedure

All resulting constructs were transformed in *Agrobacterium* strain GV3101 using a standard electroporation protocol and used for further agroinfiltration of *Nicotiana benthamiana* leaves. Equal volumes of overnight grown *Agrobacterium* cultures, $OD_{600}$ ranging from 1.8 to 2.5, were mixed and sedimented at 6000 g for 3 min. The pellet was resuspended in a solution containing 10 mM MES (pH5.5) and 10 mM $MgSO_4$, resulting in $10^{-1}$ dilution for each individual culture. Leaves of 6-8 week-old greenhouse-grown *Nicotiana benthamiana* plants were infiltrated by using a syringe without needle. In the case of using provectors for agroinfiltration, the agrobacterial mix usually carried 5 different agrobacterial strains each of them providing for one of the following components: recombinase (integrase) source (pICH10881); 5' PVX provector (pICH21380); one 3' PVX provector providing for one of the IgG chains (either pICH22250 for heavy chain or pICH22240 for light chain, depending on which complementary chain provided by TMV provector); 5' TMV provector (pICH17388); one 3' TMV provector (either pICH21910 encoding for light chain or pICH21920 encoding for heavy chain).

SDS-Page and Western Blot 100 mg samples of *N. benthamiana* leaves infiltrated with *Agrobacterium* were ground in liquid nitrogen with 300 μl protein extraction buffer (0.1M Tris, 150 mM NaCl and 0.1% Tween 20, pH8.0). Crude leaf extracts were resolved on 10% (non-reducing conditions) or 12% (reducing conditions) polyacrylamide gels using the buffer system of Laemmli followed by Coomassie Brilliant Blue staining. For Western Blot analysis, proteins from SDS-PAGE were electrophoretically transferred to a Hybond P membrane (Amersham Biosciences, UK), using Blotting Buffer (25 mM Tris, 192 mM glycin, 20% methanol, pH8.3). Membranes were blocked with 5% skim milk in TBST (50 mM Tris, 100 mM NaCl, 0.05% Tween 20, pH7.4) and probed with goat anti-human lambda light chain HRP-conjugated antibodies (Sigma, UK) or goat anti-human IgG gamma chain specific HRP-conjugated antibodies (Sigma, UK) diluted in 2.5% skim milk/TBS 1:10000 and 1:5000, respectively. Bound antibodies were detected using ECL Detection Reagent (Amersham Biosciences, UK). The results of electrophoretic separations and Western blot analyses are shown in FIG. 11B. Comparison with IgG standard showed that the yield of monoclonal antibodies in plant tissue reaches 0.2-0.35 mg per gram of fresh leaf biomass.

Isolation of Plant-Derived Recombinant Mabs

Total soluble proteins were extracted from agroinoculated *Nicotiana benthamiana* leaf areas with buffer containing 100 mM sodium phosphate, 150 mM NaCl and 0.05% Tween 20 (pH8.0). Small-scale isolation of anti-cancer mab from crude protein extracts was performed using one-step affinity purification with Protein A Magnetic Beads (New England Biolabs, USA) according to the instructions of manufacturer. Coomassie-stained gel with purified plant-derived Mab is shown in FIG. 11B (panel B).

Example 6

Expression of Follicule Stimulating Hormone (FSH) with TMV and PVX-Based Vectors The genes (cDNA) encoding for alpha (nucleotides corresponding to the coding sequences 101-463 of GenBank Acc. No. NM_173901) and beta (nucleotides corresponding to the coding sequences 70-459 of GenBank Acc. No. NM_174060) polypeptides of bovine FSH were synthesized flanked with restriction sites (5' Nco1-3'EcoR1 for FSH-alpha and FSH-beta subunits) and cloned in TMV pro-vector (pICH20431, derivative of pICH11599, FIG. 10B) and PVX vector (pICH21240), replacing the coding sequences for the heavy and light chains of IgG and generating two constructs, pICH-FSHA and pICH-FSHB, containing the sequences encoding for subunit alpha and subunit beta, respectively (FIG. 12). Mixture of agrobacteria providing for two different subunits expressed form PVX and TMV-based vectors were prepared and infiltrated into *N. benthamiana* leaves as described above and the expression level of heterodimeric FSH was measured by ELISA 10 days after inoculation using commercially available FSH dimer-specific (FSH117) antibodies and detected with Tropix chemiluminescent system (Tropix, Bedford, Mass.).

Example 7

Expression of IgM with TMV and PVX-Based Vectors

The coding sequences of GFP and DsRed in pICH15933 were replaced by the sequences encoding IgM light and J chains respectively, resulting in construct pICH-MLCJ (FIG. 13). The gene encoding for IgM heavy chain was cloned in PVX vector (pICH21240), replacing the coding sequences for IgG heavy chain and generating construct pICH-MHC (FIG. 13). Mixture of agrobacteria providing for three different chains of IgM expressed form PVX and TMV-based vectors were infiltrated into *N. benthamiana* leaves and the expression level of hetero-oligomeric complex was measured by ELISA 10 days after inoculation using commercially available IgM-specific antibodies.

The contents of European patent application No. 05 001 819.1 and of U.S. patent application No. 60/593,606, the priorities of which are claimed by the present patent application, are incorporated herein by reference in their entireties.

The invention claimed is:

1. A process of producing in a plant, in plant tissue, or in plant cells a hetero-oligomeric protein comprising at least a first and a second protein subunit, said process comprising: expressing in plant cells at least said first and said second protein subunit by providing to said plant, said plant tissue or said plant cells a first and a second plus-sense single-stranded RNA viral vector, said first viral vector encoding at least said first protein subunit, said second viral vector encoding at least said second protein subunit, wherein said first viral vector is derived from Potato Virus X and said second viral vector is derived from Tobacco Mosaic Virus.

2. The process according to claim 1, followed by isolating said hetero-oligomeric protein from said plant, said plant tissue, or said plant cells.

3. The process according to claim 1, wherein said first viral vector contains a first heterologous sequence encoding said first protein subunit and said second viral vector contains a second heterologous sequence encoding said second protein subunit, whereby expression of said first and/or of said second protein subunit is under the control of a sub-genomic promoter.

4. The process according to claim 1, wherein said first viral vector contains a first heterologous sequence encoding said first protein subunit and said second viral vector contains a second heterologous sequence encoding said second protein subunit, whereby expression of said first and/or of said second protein subunit is under the control of an IRES element.

5. The process according to claim 1, wherein said first viral vector and/or said second viral vector is/are devoid of a
  functional coat protein ORF,
  a functional movement protein ORF, and/or
  a functional origin of viral particle assembly.

6. The process according to claim 1, wherein said hetero-oligomeric protein is an antibody.

7. The process according to claim 1, wherein said viral vectors are transiently provided to said plant, plant tissue, or plant cells.

8. The process according to claim 7, wherein said viral vectors are transiently provided to said plant, plant tissue, or plant cells by *Agrobacterium* transfection.

9. The process according to claim 1, wherein said RNA viral vectors are stably incorporated into plant chromosomal DNA as DNA precursors of said RNA viral vectors.

10. The process according to claim 9, wherein controlled release of said RNA viral vectors from said DNA precursors are provided by inducible promoters.

11. The process according to claim 1, wherein at least said first or said second protein subunit has a plant-specific signal peptide as an ER-targeting signal.

12. The process according to claim 11, wherein said plant-specific signal peptides are derived from tobacco calreticulin and/or rice alpha-amylase.

13. The process according to claim 6, wherein said antibody is an immunoglobulin comprising at least a portion of an antigen binding domain.

14. The process according to claim 6, wherein said antibody comprises a protection protein in association with an immunoglobulin heavy chain, wherein the protection protein comprises a portion of a polyimmunoglobulin receptor.

15. The process according to claim 6, wherein said antibody or its derivative belongs to the immunoglobulin G class, to the immunoglobulin A class, to the immunoglobulin M class, to the immunoglobulin D class, or to the immunoglobulin E class.

16. The process according to claim 1, wherein said hetero-oligomeric protein is insulin.

17. The process according to claim 1, wherein at least one or at least two or more subunits of said hetero-oligomeric protein contain(s) an endoplasmatic reticulum retention signal KDEL.

18. The process according to claim 1, wherein said first viral vector contains a first heterologous sequence encoding said first protein subunit and said second viral vector contains a second heterologous sequence encoding said second protein subunit and wherein said heterologous nucleic acid sequences are mutated in order to partially or completely remove glycosylation sites from said hetero-oligomeric protein.

19. The process according to claim 1, wherein said plant, plant tissue or plant cell is engineered to alter the glycosylation pattern of said hetero-oligomeric protein.

20. The process according to claim 1, wherein said plant is a monocot or a dicot plant.

21. The process according to claim 20, wherein said dicot plant belongs to the Solanaceae family.

22. The process according to claim 20, wherein said dicot plant is a *Nicotiana* species.

23. The process according to claim 20, wherein said dicot plant is *Nicotiana tabacum* or *Nicotiana benthamiana*.

24. The process according to claim 20, wherein said dicot plant belongs to the Brassicaceae family.

25. The process according to claim 20, wherein said dicot plant belongs to the Legume family.

26. The process according to claim 20, wherein said dicot plant is *Medicago sativa*.

27. The process according to claim 20, wherein said dicot plant belongs to the family Chenopodiaceae.

28. The process according to claim 20, wherein said dicot plant is *Beta vulgaris*.

* * * * *